US008926981B2

(12) United States Patent
Brown

(10) Patent No.: US 8,926,981 B2
(45) Date of Patent: *Jan. 6, 2015

(54) METHODS OF USING CHIMERIC RECEPTORS TO IDENTIFY AUTOIMMUNE DISEASE

(75) Inventor: James L. Brown, Athens, OH (US)

(73) Assignee: Diagnostic Hybrids, Inc., Athens, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,819

(22) Filed: Sep. 12, 2012

(65) Prior Publication Data

US 2013/0059312 A1 Mar. 7, 2013

Related U.S. Application Data

(60) Continuation of application No. 11/906,189, filed on Oct. 1, 2007, now Pat. No. 8,293,879, which is a continuation-in-part of application No. 10/996,961, filed on Nov. 24, 2004, now abandoned, which is a division of application No. 09/539,735, filed on Mar. 30, 2000, now Pat. No. 6,852,546.

(51) Int. Cl.

| C07H 21/02 | (2006.01) |
| C07H 21/04 | (2006.01) |
| C12N 15/00 | (2006.01) |
| C12N 5/00 | (2006.01) |
| C12N 5/02 | (2006.01) |
| C12N 5/07 | (2010.01) |
| C12N 5/10 | (2006.01) |
| C07K 1/00 | (2006.01) |
| C07K 14/00 | (2006.01) |
| C07K 17/00 | (2006.01) |
| A61K 39/00 | (2006.01) |
| G01N 33/564 | (2006.01) |
| C07K 14/72 | (2006.01) |

(52) U.S. Cl.
CPC ............ G01N 33/564 (2013.01); C07K 14/721 (2013.01); C07K 2319/61 (2013.01); G01N 2800/24 (2013.01); Y10S 435/80 (2013.01)
USPC ..................... 424/185.1; 435/320.1; 435/325; 435/358; 435/362; 435/800; 530/350; 536/23.1

(58) Field of Classification Search
None
See application file for complete search history.

(56) References Cited

U.S. PATENT DOCUMENTS

| 4,609,622 | A | 9/1986 | Kohn et al. ................. 435/29 |
| 6,747,139 | B1 | 6/2004 | Rapoport et al. .......... 536/23.5 |
| 6,852,546 | B1 | 2/2005 | Brown ......................... 436/506 |
| 8,293,879 | B2 * | 10/2012 | Brown ........................ 536/23.1 |

FOREIGN PATENT DOCUMENTS

WO  WO 99/16902  4/1999

OTHER PUBLICATIONS

Abaza et al., 'Effects of amino acid substitutions outside an antigenis site on protein binding to monoclonal antibodies of predetermined specificity obtained by peptide immunization: demonstration with region 94-100 (antigenic site 3) of myoglobin,' J. Prot. Chem. 11:433-444 (1992).
Akamizu et al., 'Chimeric studies of the extracellular domain of the rat thyrotropin (TSH) receptor: amino acids (268-304) in the TSH receptor are involved in ligand high affinity binding, but not in TSH receptor-specific signal transduction,' Endocr J 40:363-372 (1993).
Baldet et al., 'Thyroid stimulating antibody: an index of thyroid stimulation in Graves' disease,' Acta Endocrinol.(Copenh) 116:7-12 (1987).
Bidey et al., 'Characterization of thyroid-stimulating immunoglobulin-induced cyclic AMP accumulation in the rat thyroid cell strain FFTL-5: potentiation by forskolin and calibration against reference preparations of thyrotrophin,' J. Endocrinol., 105:7-15 (1985).
Boshart et al., 'A very strong enhancer is located upstream of an immediate early gene of human cytomegalovirus,' Cell 41:521 (1985).
Botero and Brown, 'Bioassay of thyrotropin receptor antibodies with Chinese hamster ovary cells transfected with recombinant human thyrotropin receptor: Clinical utility in children and adolescents with Graves disease,' J. Pediatr. 132:612-618 (1998).
Coleman et al., 'Effects of amino acid sequence changes on antibody-antigen interactions,' Res. In Immunology 145:33-36 (1994).
Da Costa et al., 'Modulation of graves' disease autoantibody stimulation of recombinant human thyrotrophin receptor', Clinica. Chimica. Acata., 336: 39-44 (2003).
Dallas et al., 'Thyrotropin (TSH) receptor antibodies (TSHrAb) can inhibit TSH-mediated cyclic adenosine 3',5'-monophosphate production in thyroid cells by either blocking TSH binding or affecting a step subsequent to TSH binding,' Endocrinologu, 137(8): 332-339 (1996).
Dijkema, et al., 'Cloning and expression of the chromosomal immune interferon gene of the rat,' EMBO J. 4(3):761 (1985).
Evans et al., 'Development of a luminescent bioassay for thyroid stimulating antibodies,' J. Clin. Endocrinol. Metabol., 84:374-377 (1999).
Federman, Thyroid, in Dale and Federman (eds.), Scientific American Medicine, 3:1-6, Scientific American, New York, NY, (1997).
Gorman et al, 'The Rous sarcoma virus long terminal repeat is a strong promoter when introduced into a variety of eukaryotic cells by DNA-mediated transfection,' Proc. Natl. Acad. Sci. USA 79:6777 (1982).
Inui et al., 'Increase of thyroid stimulating activity in Graves' immunoglobulin-G by high polyethylene glycol concentrations using procine thyroid cell assay', Thyroid, 8(4): 319-325 (1998).
Kakinuma et al., 'The human thyrotropin (TSH) receptor in a TSH binding inhibition assay for TSH receptor autoantibodies,' J. Clin. Endocrinol. Metabol., 82: 2129-2134 (1997).

(Continued)

Primary Examiner — Nora Rooney
(74) Attorney, Agent, or Firm — Medlen & Carroll, LLP

(57) ABSTRACT

The present invention provides methods and compositions useful in the diagnosis and management of autoimmune diseases. In particular, the present invention provides improved methods and compositions for the diagnosis and management of Graves' disease. The methods of the present invention not only avoids the need for radioactivity and are much simpler, economical, and rapid than methods traditionally used for the diagnosis of Graves' disease, but also improve upon the sensitivity and detection abilities of previous luciferase-based autoantibody detection assays.

16 Claims, 17 Drawing Sheets

(56) References Cited

OTHER PUBLICATIONS

Kasagi et al., 'A sensitive and practical assay for thyroid-stimulating antibodies using crude immunoglobulin fractions precipitated with polyethylene glycol,' *J. Clin. Endocrinol. Metabol.*, 62:855-862 (1986).

Kim et al., 'Use of the human elongation factor 1α promoter as a versatile and efficient expression system,' *Gene* 91:217-223 (1990).

Kim et al., 'The prevalance and clinical significance of blocking thyrotropin receptor antibodies in untreated hyperthyroid graves' disease', *Thyroid* 10:579-586 (2000).

Kosugi et al., 'Mechanisms by which low salt condition increases sensitivity of thyroid stimulating antibody assay,' *Endocrinol.*, 125:410-417 (1989).

Kung et al., 'Epitope mapping of TSH receptor-blocking antibodies in graves' disease that appear during pregnancy', *J Clin Endocrinol Metab* 86:3647-3653 (2001).

Lederrnan et al., 'A single amino acid substitution in a common African allele of the cd4 molecule ablates binding of the monoclonal antibody, OKT4,' *Molec. Immunolo.* 28:1171-1181 (1991).

Maniatis, et al., 'Regulation of inducible and tissue-specific gene expression,' *Science* 236: 1237-1245 (1987).

McKenzie and Zakarija, 'Clinical review 3: the clinical use of thyrotropin receptor antibody measurements,' *J. Clin. Endocrinol. Metabol.*, 69:1093-1096 (1989).

Michelangeli et al., 'Measurement of thyroid stimulating immunoglobulins in a new cell line transfected with a functional human TSH receptor (JPO9 cells), compared with an assay using FRTL-5 cells,' *Clin. Endocrinol.*,40:645-652 (1994).

Mizushima and Nagata, 'pEF-BOS, a powerful mammalian expression vector,' *Nuc. Acids. Res.*, 18:5322 (1990).

Morganthaler et al., 'Application of a bioassay with CHO cells for the routine detection of stimulating and blocking autoantibodies to the TSH-receptor,' *Harm. Metab. Res.*, 30: 162-168 (1998).

Ochi et al., 'Augmentative effect of polyethylene glycol, polyvinyl alcohol and dextran on thyroid-stimulating antibody stimulated cAMP production in FRTL-5 cells and CHO cells expressing human TSH receptor,' *Hormone. Res.* 53:20-25 (2000).

Rapoport et al, 'Clinical experience with a human thyroid cell bioassay for thyroid-stimulating immunoglobulin,' *J. Clin. Endocrinol. Metabol.*, 58:332-338 (1984).

Sambrook et al., Molecular Cloning: A Laboratory Manual, 2nd ed., Cold Spring Harbor Laboratory Press, New York (1989), pp. 16.6-16.8.

Tahara et al., 'Immunoglobulins from graves' disease patients interact with different sites on TSH receptor/LH/CG receptor chimeras than either TSH or immunoglobulins from idiopathic myxedema patients,' *Biochem Biophys Res Comm* 179:70-77 (1991).

Uetsuki et al., 'Isolation and characterization of the human chromosomal gene for polypeptide chain elongation factor 1-α', *J. Biol. Chem.*, 264:5791 (1989).

Vitti et al., 'Detection of thyroid-stimulating antibody using Chinese hamster ovary cells transfected with cloned human thyrotropin receptor', *J. Clin. Endocrinol. Metabol.*, 76:499-503 (1993).

Voss, et al., 'The role of enhancers. In the regulation of cell-type-specific transcriptional control', *Trends Biochem. Sci.*, 11:287 (1986).

Yokoyama et al, 'Heterogeneity of graves' immunoglobulin g: comparison of thyrotropin receptor antibodies in serum and in culture supernatants of lymphocytes transformed by epstein-barr virus infection', *J. Clin. Endocrinol. Metabol.*, 64:215-218 (1987).

\* cited by examiner

```
GGCGATTTCGGAGGATGGAGAAATAGCCCCGAGTCCCGTGGAAAATGAGGCCGGCGGACTTGCTG
CAGCTGGTGCTGCTGCTCGACCTGCCCAGGGACCTGGGCGGAATGGGGTGTTCGTCTCCACCCTG
CGAGTGCCATCAGGAGGAGGACTTCAGAGTCACCTGCAAGGATATTCAACGCATCCCCAGCTTAC
CGCCCAGTACGCAGACTCTGAAGCTTATTGAGACTCACCTGAGAACTATTCCAAGTCATGCATTT
TCTAATCTGCCCAATATTTCCAGAATCTACGTATCTATAGATGTGACTCTGCAGCAGCTGGAATC
ACACTCCTTCTACAATTTGAGTAAAGTGACTCACATAGAAATTCGGAATACCAGGAACTTAACTT
ACATAGACCCTGATGCCCTCAAAGAGCTCCCCCTCCTAAAGTTCCTTGGCATTTTCAACACTGGA
CTTAAAATGTTCCCTGACCTGACCAAAGTTTATTCCACTGATATATTCTTTATACTTGAAATTAC
AGACAACCCTTACATGACGTCAATCCCTGTGAATGCTTTTCAGGGACTATGCAATGAAACCTTGA
CACTGAAGCTGTACAACAATGGCTTTACTTCAGTCCAAGGATATGCTTTCAATGGGACAAAGCTG
GATGCTGTTTACCTAAACAAGAATAAATACCTGACAGTTATTGACAAAGATGCATTTGGAGGAGT
ATACAGTGGACCAAGCTTGCTGGACGTGTCTCAAACCAGTGTCACTGCCCTTCCATCCAAAGGCC
TGGAGCACCTGAAGGAACTGATAGCAAGAAACACCTGGACTCTTAAGACACTGCCCTCCAAAGAA
AAATTCACGAGCCTCCTGGTCGCCACGCTGACCTACCCCAGCCACTGCTGCGCCTTCAG*TAATT
TGCCGAAGAAAGAACAGAATTTTTCATTTTCCATTTTTGAAAACTTCTCCAAACAATGCGAAAGC
ACAGTTAGAAAAGCAGATAACGAGACGCTTTATTCCGCCATCTTTGAGGAGAATGAACTCAGTGG
CTGGGATGAGCTCAAAAACCCCCAGGAAGAGACTCTACAAGCTTTTGACAGCCATTATGACTACA
CCATATGTGGGGACAGTGAAGACATGGTGTGTACCCCCAAGTCCGATGAGTTCAACCCGTGTGAA
GACATAATGGGCTACAAGTTCCTGAGAATTGTGGTGTGGTTCGTTAGTCTGCTGGCTCTCCTGGG
CAATGTCTTTGTCCTGCTTATTCTCCTCACCAGCCACTACAAACTGAACGTCCCCCGCTTTCTCA
TGTGCAACCTGGCCTTTGCGGATTTCTGCATGGGGATGTACCTGCTCCTCATCGCCTCTGTAGAC
CTCTACACTCACTCTGAGTACTACAACCATGCCATCGACTGGCAGACAGGCCCTGGGTGCAACAC
GGCTGGTTTCTTCACTGTCTTTGCAAGCGAGTTATCGGTGTATACGCTGACGGTCATCACCCTGG
AGCGCTGGTATGCCATCACCTTCGCCATGCGCCTGGACCGGAAGATCCGCCTCAGGCACGCATGT
GCCATCATGGTTGGGGCTGGGTTTGCTGCTTCCTTCTCGCCCTGCTTCCTTTGGTGGGAATAAG
TAGCTATGCCAAAGTCAGTATCTGCCTGCCCATGGACACCGAGACCCCTCTTGCTCTGGCATATA
TTGTTTTTGTTCTGACGCTCAACATAGTTGCCTTCGTCATCGTCTGCTGCTGTTATGTGAAGATC
TACATCACAGTCCGAAATCCGCAGTACAACCCAGGGGACAAAGATACCAAAATTGCCAAGAGGAT
GGCTGTGTTGATCTTCACCGACTTCATATGCATGGCCCCAATCTCATTCTATGCTCTGTCAGCAA
TTCTGAACAAGCCTCTCATCACTGTTAGCAACTCCAAAATCTTGCTGGTACTCTTCTATCCACTT
AACTCCTGTGCCAATCCATTCCTCTATGCTATTTTCACCAAGGCCTTCCAGAGGGATGTGTTCAT
CCTACTCAGCAAGTTTGGCATCTGTAAACGCCAGGCTCAGGCATACCGGGGGCAGAGGGTTCCTC
CAAAGAACAGCACTGATATTCAGGTTCAAAAGGTTACCCACGACATGAGGCAGGGTCTCCACAAC
ATGGAAGATGTCTATGAACTGATTGAAAACTCCCATCTAACCCCAAAGAAGCAAGGCCAAATCTC
AGAAGAGTATATGCAAACGGTTTTGTAAGTTAACACTACACTACTCACAATGGTAGGGAACTTA
CAAAATAATAGTTTCTTGAATATGCATTCCAATCCCATGACACCCCCAAC
```

Figure 8

```
human PGH al      1 ---------------atgtgtatggctcaataaaattac
HEK M13R seq      1 attcgcccttgagctcatgtgtatggctcaataaaattac human PGH al     25 gtacaaagtgacagcgtactctcttttcatgggctgacct
HEK M13R seq     41 gtacaaagtgacagcgtactctcttttcatgggctgacct human PGH al     65 tgtcgtcaccatcacctgaaaatggctccaaacaaaaatg
HEK M13R seq     81 tgtcgtcaccatcacctgaaaatggctccaaacaaaaatg human PGH al    105 acctaagggttgaaacaagataagatcaaattgacgtcat
HEK M13R seq    121 acctaagggttgaaacaagataagatcaaattgacgtcat human PGH al    145 ggtaaaaattgacgtcatggtaattacaccaagtacoctt
HEK M13R seq    161 ggtaaaaattgacgtcatggtaattacaccaagtaccctt human PGH al    185 caatcattggatggaatttcctgttgatcccagggcttag
HEK M13R seq    201 caatcattggatggaatttcctgttgatcccagggcttag human PGH al    225 atgcaggtggaaacactctgctggtataaaagcaggtgac
HEK M13R seq    241 atgcaggtggaaacactctgctggtataaaagcaggtgag human PGH al    265 gacttcattatactgcagttactgagaactcataagacga
HEK M13R seq    281 gacttcattatactgcagttactgagaactcataagacga human PGH al      -----------------
HEK M13R seq    321 agatctaagggcgaatt
```

Figure 9

A
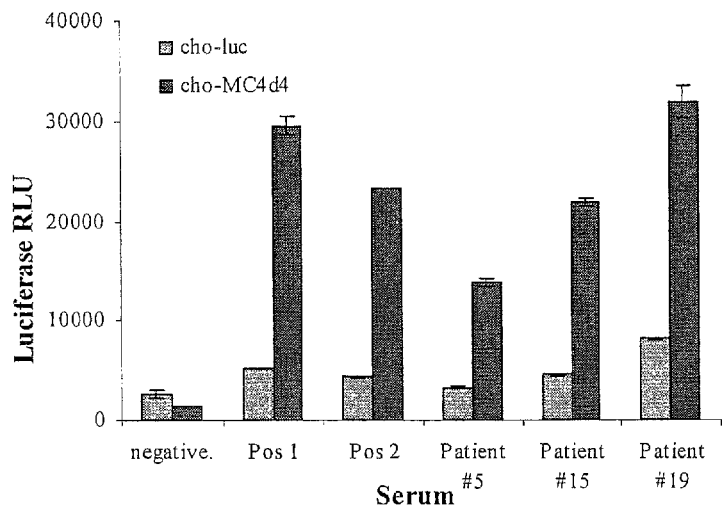
B
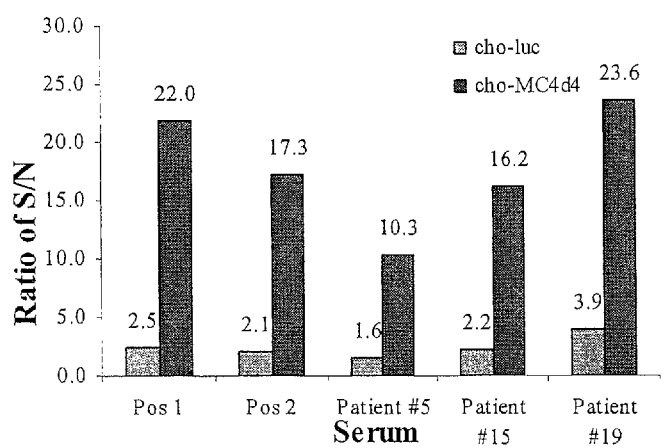
Figure 10

C
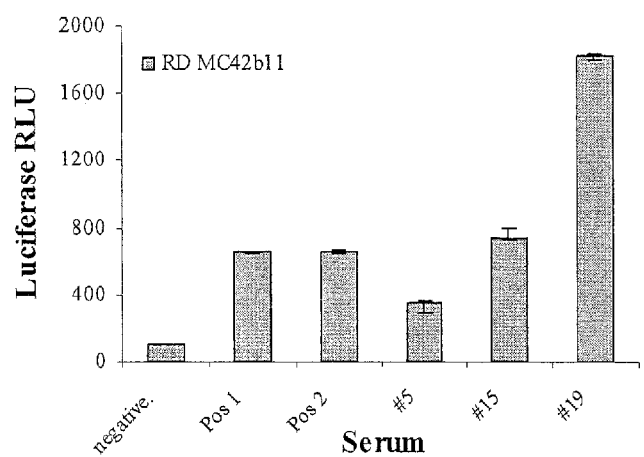
D
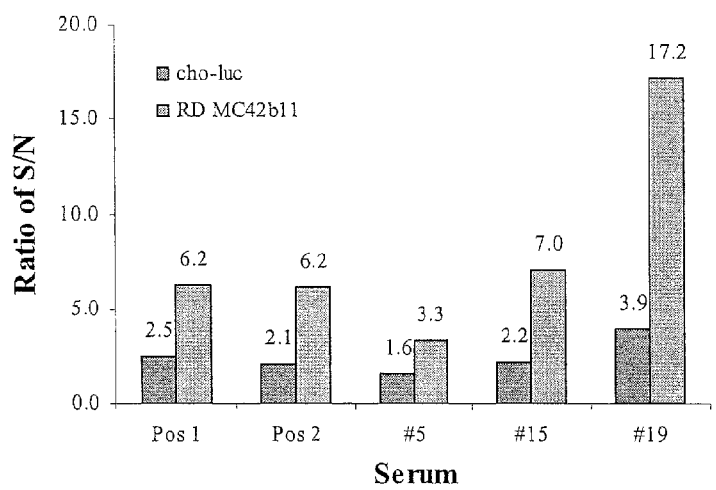
Figure 10 (Cont'd)

E

A
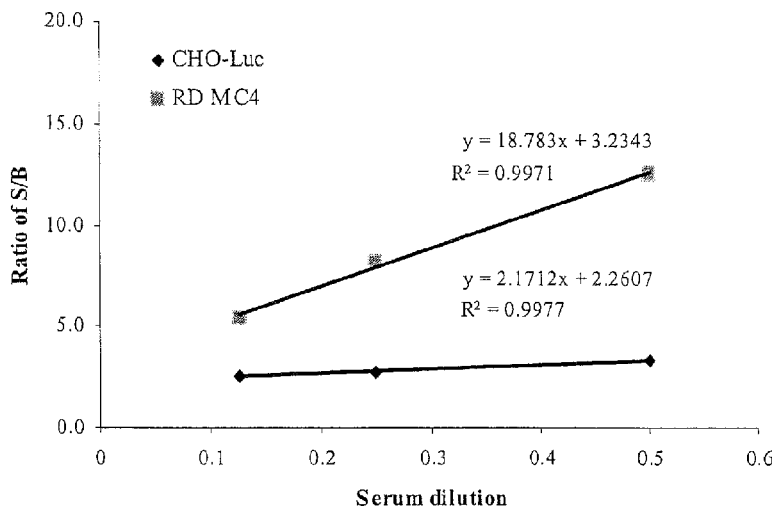
B
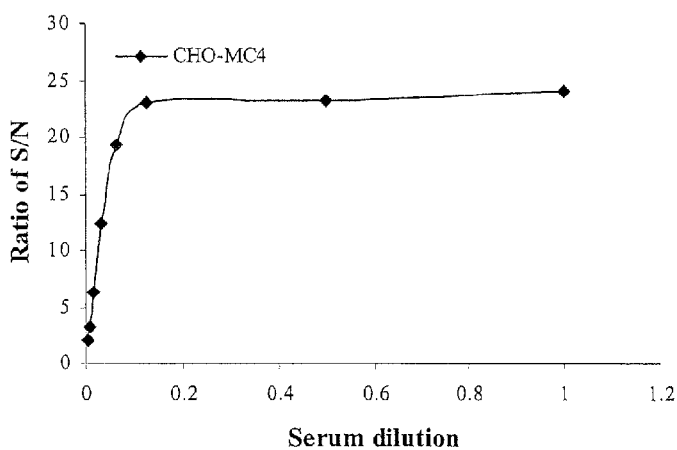
C
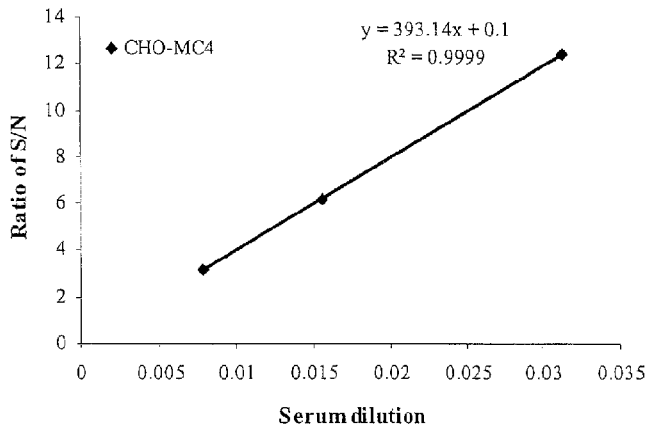
Figure 11

A 1 qtliatssys lkklpsrekf anlldatlty pshccafrnv ptkeqnfsfs isknfpkqce
61 stvrkqnnet lypaifaesg qsgwd

B 1 ililntknll hiedgafrnl prlkylsicn tgiiefpdlt qifsseahfi lelcdnlrmt
61 tipqnafrgm snesltlkly kngfedihsh afngtklnql ilkdnknlrr ihndalrgai
121 gpdvldisst aleslpsygl eaiqvlngms syslkrlppl dkfsslleav lty

C 1 mlpallplll pallpgaggg rcpqrcactq palrcptppp garpaparas fthlpvkvip
61 shafeglrda fiieisqsds lerieasafd slpalseili lntknllhie dgafrnlprl
121 kylsicntgi iefpdltqif sseahfilel cdnlrmttip qnafqgmsne sltlklykng
181 fedihshafn gtklnqlilk dknnlrrihn dalrgatgpd vldisstale slpsygleai
241 qvlnamssys lkrlppldkf sslleavlty pshccafqnl rtekqnslls ifdnfskqce
301 stmrkpasev fyrdassnts lwpaekhmyp letgeeafpy systvfyede mtgfdfeydf
361 cqpkiltctp epdafnpccd ilgysflrvl iwfinilala gnfivllvli tshykltvpr
421 flmcnlsfad fcmglyllli asvdaqtsgq yynhaidwqt gsgcstagff tvfaselsvy
481 tltvitierw htityamqld rklrlrhavp imlggwvfsi liavlpllgv ssymkvsicl
541 pmdietglsq ayillilmln viaflvicac yikiyvavqn pelvaankdt kiakrmaili
601 ftdftcmapi sffaisaaik vplitvtnsk illvlfypvn scanpflyai ftkafqrdff
661 llmsklgcck sraelyrvny fsaytpnckn gssapgpska sqallllsas eklcktrrst
721 kksqpecq

D 1 mgrrvpalrq llvlamlvlk qsqlhspels gsrcpepcdc apdgalrcpg praglarl

E 1 mgrpslalrl llallllppp apllwalrpa pcpepcscpp dgalrcpgpq aglsrlslty
61 lpikvipsqa frglneviki eisqsdslek ieanafdnll nlseiliqnt knlvhieaga
121 ftnlprlkyl sicntgihkl pdvtkifsse fnfileicdn lhittiprna fqgmmnesit
181 lklygngfee iqshafngtt lislelkena rlekmhndaf rgatgpsild isstklqalp
241 tyglesiqtl iatssyslkk lpsrekftnl ldatltypsh ccafrnlptn eqnfsfsifk
301 nfskqcesta rrpnnetlys aifaeselsg wdydygfclp ktlqcapepd afnpcedimg
361 ynflrvliwl inilaitgnv tvlfvlltsr ykltvprflm cnlsfadfcm glyllliasv
421 daqtkgqyyn haidwqtgsg csaagfftvf aselsvytlt vitlerwhti tyaiqldqkl
481 rlkhaipvml ggwlfstlia vlplvgvsny mkvsiclpmd vestlsqvyi ltililnvma
541 fiiicacyik iyfavqnpel matnkdtkia kkmavliftd ftcmapisff aisaafkvpl
601 itvtnskvll vlfypvnsca npflyaiftk afqrdfflll skfgcckyra elyrrkdfsa
661 yisnckngft gsnkpsrstf klttlqcqys avldktcyke c

Figure 15

METHODS OF USING CHIMERIC RECEPTORS TO IDENTIFY AUTOIMMUNE DISEASE

This is a Continuation of patent application Ser. No. 11/906,189 filed on Oct. 1, 2007 (now issued as U.S. Pat. No. 8,293,879), which is a Continuation-In-Part of patent application Ser. No. 10/996,961 filed on Nov. 24, 2004 (now abandoned) which is a Divisional of patent application Ser. No. 09/539,735 filed on Mar. 30, 2000 (now issued as U.S. Pat. No. 6,852,546).

FIELD OF THE INVENTION

The present invention provides methods and compositions useful in the diagnosis of autoimmune diseases. In particular, the present invention provides methods and compositions for use in the diagnosis and management of Graves' disease.

BACKGROUND OF THE INVENTION

Graves' disease (also referred to as "diffuse toxic goiter"), is the leading cause of hyperthyroidism due to the action of autoantibodies that recognize and bind to receptors present on the thyroid gland, resulting in gland growth and over-production of thyroid hormone. Graves' disease is reported to be the most frequent cause of hyperthyroidism in childhood and adolescence (See, Boter and Brown, J. Pediatr. 132:612-618 (1998)).

Current diagnostic techniques for Graves' disease leave much to be desired. In general, the commercially available methods are cumbersome and laborious. Other method require the administration of radioactive tracers to the person requiring a diagnosis. Most importantly, however, the vast majority of the presently used methods lack sufficient sensitivity such that a quick, accurate and cost-effective test can be performed.

What is still needed is an assay system for Graves' disease that is safe, easy to use, sensitive, specific, and cost-effective.

SUMMARY OF THE INVENTION

The present invention provides methods and compositions useful in the diagnosis and management of autoimmune diseases. In particular, the present invention provides methods and compositions for the diagnosis and management of Graves' disease.

In one embodiment, the present invention contemplates a nucleotide vector comprising a first nucleotide sequence encoding a chimeric TSH receptor and a second nucleotide sequence encoding a luciferase gene. In one embodiment, the vector further comprises a promoter operably linked to the first and second nucleotide sequences. In one embodiment, the chimeric TSH receptor comprises an amino acid sequence derived from rat chorionic hormone gonadotropin receptor. In one embodiment, the first nucleotide sequence encodes a human TSH receptor wherein amino acid residues 262-335 are derived from a rat lutenizing hormone chorionic gonadotropin receptor. In one embodiment, the promoter comprises a glycoprotein alpha subunit promoter. In one embodiment, the luciferase gene is derived from a *Renilla* firefly.

In one embodiment, the present invention contemplates a cell line comprising a stably transfected vector encoding a chimeric TSH receptor and a luciferase gene. In one embodiment, the vector further comprises a promoter operably linked to the vector. In one embodiment, the promoter comprises a glycoprotein alpha subunit promoter. In one embodiment, the chimeric TSH receptor comprises an amino acid sequence derived from rat chorionic hormone gonadotropin receptor. In one embodiment, the vector encodes a human TSH receptor wherein amino acid residues 262-335 are derived from a rat lutenizing hormone chorionic gonadotropin receptor amino acid sequence. In one embodiment, the cell line comprises CHO cells. In one embodiment, the cell line comprises RD cells.

In one embodiment, the present invention contemplates a method, comprising: a) providing; i) a cell line comprising a stably transfected vector encoding a chimeric TSH receptor and a luciferase gene; ii) a serum sample derived from a patient suspected of having Graves' disease; b) contacting the serum sample with said cell line under conditions such that the luciferase gene emits a detectable signal. In one embodiment, the method further comprises step c) measuring the signal intensity, wherein the intensity correlates with a thyrotropin stimulating hormone receptor autoantibody concentration present in the sample. In one embodiment, the contacting further comprises polyethylene glycol. In one embodiment, the chimeric TSH receptor comprises an amino acid sequence derived from rat chorionic hormone gonadotropin receptor. In one embodiment, the amino acid sequence comprises seventy three amino acids corresponding to amino acid residues 262-335 of a human TSH receptor amino acid sequence. In one embodiment, the serum sample comprises TSH receptor autoantibodies. In one embodiment, the autoantibodies comprise TSH stimulating autoantibodies. In one embodiment, the autoantibodies comprise TSH blocking antibodies.

In one embodiment, the present invention contemplates a kit comprising comprising a chimeric TSH receptor and a luciferin-luciferase system capable of detecting serum TSH autoantibodies. In one embodiment, the receptor comprises a human TSH amino acid sequence. In one embodiment, the receptor comprises a rat TSH amino acid sequence. In one embodiment, the rat TSH amino acid sequence comprises amino acid residues 262-335. In one embodiment, the kit further comprises a cell line capable of expressing the chimeric TSH receptor and the luciferin-luciferase system. In one embodiment, the kit further comprises polyethylene glycol. In one embodiment, the kit comprises a vector encoding the chimeric TSH receptor and a luciferase gene. In one embodiment, the vector further comprises a promoter in operably linked to the vector. In one embodiment, the promoter comprises a glycoprotein alpha subunit promoter. In one embodiment, the cell line comprises CHO cells. In one embodiment, the cell line comprises RD cells. In one embodiment, the kit further comprises an instruction sheet.

In one embodiment, the present invention provides methods for determining the presence of thyroid-stimulating autoantibodies in a test sample, comprising: a) providing i) a test sample suspected of containing thyroid-stimulating autoantibodies, ii) cultured cells contained within a testing means, wherein the cells express a chimeric TSH receptor and a luciferin-luciferase system, and iii) polyethylene glycol; b) exposing the test sample to the cultured cells and polyethylene glycol under conditions such that thyroid-stimulating antibodies are detectable using a luciferin-luciferase system; and c) observing for the presence of detectable thyroid-stimulating antibodies. In one preferred embodiment, the cultured cells are selected from the group consisting of RDluc and CHORluc cells. In another embodiment, the observing is conducted using a luminometer. In further embodiments, the cAMP concentration is determined by the luciferin-luciferase system. In yet another embodiment, the methods further comprises a Growth Medium, while in other embodiments, the methods further comprises a Stimulation Medium. In some particularly preferred embodiments, the cultured cells are exposed to the Growth Medium prior to exposure of the test sample. In still further embodiments, the cultured cells are exposed to Stimulation Medium after exposure to the test sample. In other particularly preferred embodiments, the Stimulation Medium comprises polyethylene glycol.

The present invention also provides methods for determining the presence of thyroid-stimulating autoantibodies in a test sample, comprising: a) providing; i) a test sample suspected of containing thyroid-stimulating autoantibodies, ii) cultured cells selected from the group consisting of RD-Rluc and CHO-Rluc cells contained within a testing means, wherein the cells express a chimeric TSH receptor, and iii) polyethylene glycol; b) exposing the test sample to the cultured cells and the polyethylene glycol under conditions such that thyroid stimulating antibodies are detectable using a luciferin-luciferase system; and c) observing for the presence of detectable thyroid-stimulating antibodies, wherein observing is conducted using a luminometer. In further embodiments, the cAMP concentration is determined by the luciferin-luciferase system. In some embodiments, the methods further comprise a Growth Medium, while in other embodiments the methods further comprise a Stimulation Medium. In some particularly preferred embodiments, the cultured cells are exposed to the Growth Medium prior to exposure of the test sample. In still other embodiments, the cultured cells are exposed to the Stimulation Medium after exposure to the test sample. In yet other preferred embodiments, the Stimulation Medium comprises polyethylene glycol.

The present invention also provides methods for determining the presence of thyroid-stimulating autoantibodies in a test sample, comprising: a) providing; i) a test sample suspected of containing thyroid-stimulating autoantibodies, ii) cultured cells selected from the group consisting of RD-Rluc and CHO-Rluc cells contained within a testing means, wherein the cell express a chimeric TSH receptor, iii) Growth Medium, and iv) Stimulation Medium, wherein the Stimulation Medium comprises polyethylene glycol; b) exposing the cultured cells to Growth Medium to produce grown cells; c) exposing the test sample to the grown cells and Stimulation Medium under conditions such that thyroid-stimulating antibodies are detectable using the luciferin-luciferase system; and d) observing for the presence of detectable thyroid-stimulating antibodies, wherein said observing is conducted using a luminometer. In further embodiments, the cAMP concentration is determined by the luciferase-luciferin system.

BRIEF DESCRIPTION OF THE FIGURES

FIG. 8 (SEQ ID NO:3) shows one embodiment of a DNA sequence for a chimeric hTSH/mLH (Mc4) receptor comprising 2,324 base pairs and encoding 730 amino acids. The underlined letters are the human TSHR sequence. The letters in italics are the rat LHR sequence. "*" (T) in the rat LHR sequence is a G in the wild type sequence. This G to T mutation resulted in an amino acid change from Arginine to Serine.

FIG. 9 (SEQ ID NOS:4-5) shows one embodiment of a 236 nucleotide glycoprotein alpha subunit promoter comprising a cyclic AMP (cAMP) regulatory element (CRE) (AF401991) sequence alignment with a GPH promoter amplified by PCR from HEK cells. Shaded areas indicate homology. Non-highlighted areas designate the flanking region of the promoter in the plasmid.

FIG. 10A: Luciferase assay on CHO-Luc and CHO-MC4 cell lines induced with TSI negative and positive sera.

FIG. 10B: The ratio of S/N derived from the luciferase assay on CHO-Luc and CHO-MC4 cell lines induced with TSI negative and positive sera.

FIG. 10C: Luciferase assay on CHO-Luc and RD-MC4 cell lines induced with TSI negative and positive sera.

FIG. 10D: The ratio of S/N derived from the luciferase assay on CHO-Luc and RD-MC4 cell lines induced with TSI negative and positive sera.

FIG. 10E: The ratio of S/N derived from the luciferase assay on CHO-Luc, CHO-MC4 and RD-MC4 cell lines induced with TSI negative and positive sera.

FIG. 11 presents exemplary data showing signal-to-noise (S/N) ratios for RD-MC4 and CHO-Luc cell lines in response to a serum dilution profile.

FIG. 11A: The S/N ratio from the luciferase assay on CHO-Luc and RD-MC4 cell lines induced with same dilutions of the TSI positive serum.

FIG. 11B: The S/N ratio from the luciferase assay on CHO-MC4 cell line induced with dilution of the TSI positive serum.

FIG. 11C: The S/N ratio from the luciferase assay on CHO-MC4 cell line induced with higher dilutions of the TSI positive

FIG. 15 presents exemplary amino acid sequences: lutenizing hormone receptor:

FIG. 15A: *Callithrix jacchus* (white-tufted-ear marmoset) CAJ57370 (SEQ ID NO:6)

FIG. 15B: *Coturnix japonica* (Japanese quail) AAB32614 (SEQ ID NO:7)

FIG. 15C: *Gallus gallus* (chicken) NP_990267 (SEQ ID NO:8)

FIG. 15D: *Mus musculus* (mouse) AAB24402 (SEQ ID NO:9)

FIG. 15E: *Bos taurus* (cow) NP__776806 (SEQ ID NO:10)

DEFINITIONS

Figure 1:
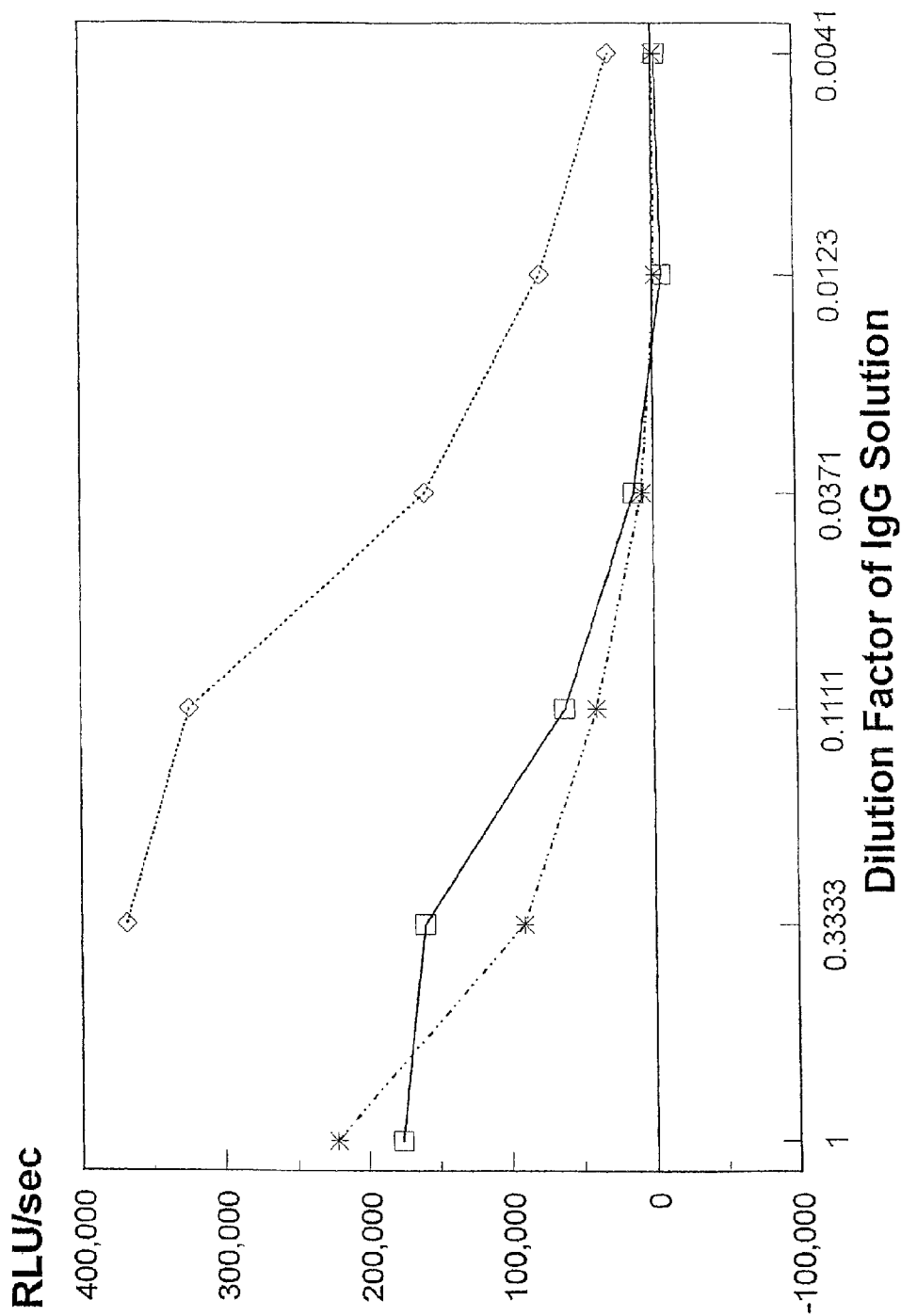
FIG. 1 provides results for serial 3-fold dilutions of three Graves' disease IgG samples (from untreated Graves' patients), in assays utilizing Stimulation Medium containing 6% PEG-8000.

The terms "sample" and "specimen" in the present specification and claims are used in their broadest sense. On the one hand, they are meant to include a specimen or culture. On the other hand, they are meant to include both biological and environmental samples. These terms encompass all types of samples obtained from humans and other animals, including but not limited to, body fluids (e.g., blood), as well as solid tissue.

Biological samples may be animal, including human, fluid or tissue, food products and ingredients such as dairy items, vegetables, meat and meat by-products, and waste. These examples are not to be construed as limiting the sample types applicable to the present invention.

As used herein, the term "kit" is used in reference to a combination of reagents and other materials.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.).

As used herein, the term "antigen" is used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen (immunogen) or portion of an antigen.

As used herein, the terms "antigen fragment" and "portion of an antigen" are used in reference to a portion of an antigen. Antigen fragments or portions may occur in various sizes, ranging from a small percentage of the entire antigen to a large percentage, but not 100% of the antigen. However, in situations where at least a portion of an antigen is specified, it is contemplated that the entire antigen may be present. It is contemplated that antigen fragments or portions, may, but are not required to comprise an "epitope" recognized by an antibody. Antigen fragments or portions also may or may not be immunogenic.

As used herein, the term "autoantibodies" refers to antibodies that are capable of reacting against an antigenic constituent of an individual's own tissue or cells (e.g., the antibodies recognize and bind to "self" antigens).

As used herein, the term "immunoassay" is used in reference to any method in which antibodies are used in the detection of an antigen. It is contemplated that a range of immunoassay formats be encompassed by this definition, including but not limited to, direct immunoassays, indirect immunoassays, and "sandwich" immunoassays." However, it is not intended that the present invention be limited to any particular format. It is contemplated that other formats, including radioimmunoassays (RIA), immunofluorescent assays (IFA), and other assay formats, including, but not limited to, variations on the ELISA, RIA and/or IFA methods will be useful in the method of the present invention.

As used herein, the term "capture antibody" refers to an antibody that is used to bind an antigen and thereby permit the recognition of the antigen by a subsequently applied antibody. For example, the capture antibody may be bound to a microtiter well and serve to bind an antigen of interest present in a sample added to the well. Another antibody (termed the "primary antibody") is then used to bind to the antigen-antibody complex, in effect to form a "sandwich" comprised of antibody-antigen-antibody complex. Detection of this complex can be performed by several methods. The primary antibody may be prepared with a label such as biotin, an enzyme, a fluorescent marker, or radioactivity, and may be detected directly using this label. Alternatively, a labelled "secondary antibody" or "reporter antibody" which recognizes the primary antibody may be added, forming a complex comprised of an antibody-antigen-antibody-antibody complex. Again, appropriate reporter reagents are then added to detect the labelled antibody. Any number of additional antibodies may be added as desired. These antibodies may also be labelled with a marker, including, but not limited to an enzyme, fluorescent marker, or radioactivity.

As used herein, the term "reporter reagent" or "reporter molecule" is used in reference to compounds which are capable of detecting the presence of antibody bound to antigen. For example, a reporter reagent may be a colorimetric substance attached to an enzymatic substrate. Upon binding of antibody and antigen, the enzyme acts on its substrate and causes the production of a color. Other reporter reagents include, but are not limited to, fluorogenic and radioactive compounds or molecules. This definition also encompasses the use of biotin and avidin-based compounds (e.g., including, but not limited to, neutravidin and streptavidin) as part of the detection system. In one embodiment of the present invention, biotinylated antibodies may be used in the present invention in conjunction with avidin-coated solid support.

As used herein the term "signal" is used in reference to an indicator that a reaction has occurred, for example, binding of antibody to antigen. It is contemplated that signals in the form of radioactivity, fluorogenic reactions, luminscent and enzymatic reactions will be used with the present invention. The signal may be assessed quantitatively as well as qualitatively.

As used herein the term "signal intensity" refers to magnitude of the signal strength wherein the intensity correlates with the amount of reaction substrate. For example, a luciferin-luciferase system generates a signal intensity that correlates with the amount of cAMP generated by thyrotropin stimulating hormone receptor autoantibodies.

As used herein, the term "luciferin-luciferase system" refers to any process or method that allows the contact of luciferin and luciferase in the presence of a substrate (i.e., for example, cAMP) under conditions such that the resulting luminesence may be detected. Such a system may be comprised within a transfected host cell encoded by a vector, or provided in separate kit containers whereby the contents may be mixed together.

As used herein, the term "solid support" is used in reference to any solid material to which reagents such as antibodies, antigens, and other compounds may be attached. For example, in the ELISA method, the wells of microtiter plates often provide solid supports. Other examples of solid supports include microscope slides, coverslips, beads, particles, cell culture flasks, as well as many other items.

As used herein, the term "cell staining" is used in reference to methods used to label or stain cells to enhance their visualization. This staining or labelling may be achieved through the use of various compounds, including but not limited to, fluorochromes, enzymes, gold, and iodine. It is contemplated that the definition encompasses such methods as "in situ chromogenic assays," in which a test (i.e., an assay) is conducted on a sample in situ. It is also contemplated that the in situ chrdmogenic assay will involve the use of an immunoassay (i.e., an ELISA).

As used herein, the term "Growth Medium" refers to a culture medium formulated to contain various growth factors including, but not limited to, vitamins, amino acids, co-factors, and any other appropriate nutrients to enhance growth and replication of cells in culture.

As used herein, the term "Stimulation Medium" refers to a medium formulated to be deficient in certain constituents (e.g., sodium chloride), in order to enhance the stimulation of by TSH and/or TSI, thereby increasing the resulting signal (e.g., cAMP and/or luciferase).

As used herein, the term "Starvation Medium" refers to a medium formulated to be deficient in at least one growth factors included in the Growth Medium. In preferred embodiments, this medium contains only the salts and glucose necessary to sustain cells for a short period of time.

As used herein, the term "organism" and "microorganism," are used to refer to any species or type of microorganism, including but not limited to viruses and bacteria, including rickettsia and chlamydia. Thus, the term encompasses, but is not limited to DNA and RNA viruses, as well as organisms within the orders Rickettsiales and Chlamydiales.

As used herein, the term "culture," refers to any sample or specimen which is suspected of containing one or more microorganisms. "Pure cultures" are cultures in which the organisms present are only of one strain of a particular genus and species. This is in contrast to "mixed cultures," which are cultures in which more than one genus and/or species of microorganism are present.

As used herein, the term "cell type," refers to any cell, regardless of its source or characteristics.

As used herein, the terms "cell line," refers to cells that are cultured in vitro, including primary cell lines, finite cell lines, continuous cell lines, and transformed cell lines.

As used herein, the terms "primary cell culture," and "primary culture," refer to cell cultures that have been directly obtained from animal or insect tissue. These cultures may be derived from adults as well as fetal tissue.

As used herein, the term "finite cell lines," refer to cell cultures that are capable of a limited number of population doublings prior to senescence.

As used herein, the term "continuous cell lines," refer to cell cultures that have undergone a "crisis" phase during which a population of cells in a primary or finite cell line apparently ceases to grow, but yet a population of cells emerges with the general characteristics of a reduced cell size, higher growth rate, higher cloning efficiency, increased tumorigenicity, and a variable chromosomal complement. These cells often result from spontaneous transformation in vitro. These cells have an indefinite lifespan.

As used herein, the term "transformed cell lines," refers to cell cultures that have been transformed into continuous cell lines with the characteristics as described above. Transformed cell lines can be derived directly from tumor tissue and also by in vitro transformation of cells with whole virus (e.g., SV40 or EBV), or DNA fragments derived from a transforming virus using vector systems.

As used herein, the term "hybridomas," refers to cells produced by fusing two cell types together. Commonly used hybridomas include those created by the fusion of antibody-secreting B cells from an immunized animal, with a malignant myeloma cell line capable of indefinite growth in vitro. These cells are cloned and used to prepare monoclonal antibodies.

As used herein, the term "mixed cell culture," refers to a mixture of two types of cells. In some preferred embodiments, the cells are cell lines that are not genetically engineered, while in other preferred embodiments the cells are genetically engineered cell lines. In some embodiments, the one or more of the cell types is "permissive" (i.e., virus is capable of replication and spread from cell to cell within the culture). The present invention encompasses any combination of cell types suitable for the detection, identification, and/or quantitation of viruses in samples, including mixed cell cultures in which all of the cell types used are not genetically engineered, mixtures in which one or more of the cell types are genetically engineered and the remaining cell types are not genetically engineered, and mixtures in which all of the cell types are genetically engineered.

As used herein, the term "suitable for the detection of intracellular parasites," refers to cell cultures that can be successfully used to detect the presence of an intracellular parasite in a sample. In preferred embodiments, the cell cultures are capable of maintaining their susceptibility to infection and/or support replication of the intracellular parasite. It is not intended that the present invention be limited to a particular cell type or intracellular parasite.

As used herein, the term "susceptible to infection" refers to the ability of a cell to become infected with virus or another intracellular organism. Although it encompasses "permissive" infections, it is not intended that the term be so limited, as it is intended that the term encompass circumstances in which a cell is infected, but the organism does not necessarily replicate and/or spread from the infected cell to other cells. The phrase "viral proliferation," as used herein describes the spread or passage of infectious virus from a permissive cell type to additional cells of either a permissive or susceptible character.

As used herein, the terms "monolayer," "monolayer culture," and "monolayer cell culture," refer to cells that have adhered to a substrate and grow as a layer that is one cell in thickness. Monolayers may be grown in various vessels including, but not limited to, flasks, tubes, coverslips (e.g., shell vials), roller bottles, etc. Cells may also be grown attached to microcarriers, including but not limited to beads.

As used herein, the term "suspension," and "suspension culture," refers to cells that survive and proliferate without being attached to a substrate. Suspension cultures are typically produced using hematopoietic cells, transformed cell lines, and cells from malignant tumors.

As used herein, the terms "culture media," and "cell culture media," refers to media that are suitable to support the growth of cells in vitro (i.e., cell cultures). It is not intended that the term be limited to any particular culture medium. For example, it is intended that the definition encompass outgrowth as well as maintenance media. Indeed, it is intended that the term encompass any culture medium suitable for the growth of the cell cultures of interest.

As used herein, the term "obligate intracellular parasite," (or "obligate intracellular organism") refers to any organism which requires an intracellular environment for its survival and/or replication. Obligate intracellular parasites include viruses, as well as many other organisms, including certain bacteria including, but not limited to, most members of the orders: i) Rickettsiales: for example, *Coxiella*, *Rickettsia* and *Ehrlichia*; and ii) Chlamydiales: for example, *C. trachomatis*, *C. psittaci*. The term "intracellular parasite," refers to any organism that may be found within the cells of a host animal, including but not limited to obligate intracellular parasites briefly described above. For example, intracellular parasites include organisms such as *Brucella*, *Listeria*, *Mycobacterium* (e.g., *M. tuberculosis* and *M. leprae*), and *Plasmodium*, as well as *Rochalirnea*.

As used herein, the term "antimicrobial," is used in reference to any compound which inhibits the growth of, or kills microorganisms. It is intended that the term be used in its broadest sense, and includes, but is not limited to compounds such as antibiotics which are produced naturally or synthetically. It is also intended that the term includes compounds and elements that are useful for inhibiting the growth of, or killing microorganisms.

As used herein, the terms "chromogenic compound," and "chromogenic substrate," refer to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the commonly used meaning of the terms "pH indicator," "redox indicator," and "oxidation-reduction indicator," are intended. Thus, "pH indicator," encompasses all compounds commonly used for detection of pH changes, including, but not limited to phenol red, neutral red, bromthymol blue, bromcresol purple, bromcresol green, bromchlorophenol blue, m-cresol purple, thymol blue, bromcresol purple, xylenol blue, methyl red, methyl orange, and cresol red. The terms "redox indicator," and "oxidation-reduction indicator," encompasses all compounds commonly used for detection of oxidation/reduction potentials (i.e., "eH") including, but not limited to various types or forms of tetrazolium, resazurin, and methylene blue.

As used herein, the term "inoculating suspension," or "inoculant," is used in reference to a suspension which may be inoculated with organisms to be tested. It is not intended that the term "inoculating suspension," be limited to a particular fluid or liquid substance. For example, inoculating suspensions may be comprised of water, saline, or an aqueous solution. It is also contemplated that an inoculating suspension may include a component to which water, saline or any aqueous material is added. It is contemplated in one embodiment, that the component comprises at least one component useful for the intended microorganism. It is not intended that the present invention be limited to a particular component.

As used herein, the term "primary isolation," refers to the process of culturing organisms directly from a sample. As used herein, the term "isolation," refers to any cultivation of organisms, whether it be primary isolation or any subsequent cultivation, including "passage," or "transfer," of stock cultures of organisms for maintenance and/or use.

As used herein, the term "presumptive diagnosis," refers to a preliminary diagnosis which gives some guidance to the treating physician as to the etiologic organism involved in the patient's disease. Presumptive diagnoses are often based on "presumptive identifications," which as used herein refer to the preliminary identification of a microorganism.

As used herein, the term "definitive diagnosis," is used to refer to a final diagnosis in which the etiologic agent of the patient's disease has been identified. The term "definitive identification" is used in reference to the final identification of an organism to the genus and/or species level.

The term "recombinant DNA molecule," as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region (enhancer elements can exert their effect even when located 3' of the promoter element and the coding region). Transcription termination and polyadenylation signals are located 3' or downstream of the coding region.

The term "an oligonucleotide having a nucleotide sequence encoding a gene," refers to a DNA sequence comprising the coding region of a gene or, in other words, the DNA sequence which encodes a gene product. The coding region may be present in either a cDNA or genomic DNA form. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the vectors of the present invention may contain endogenous enhancers and/or promoters, splice junctions, intervening sequences, polyadenylation signals, etc. or a combination of both endogenous and exogenous control elements.

The term "transcription unit," as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "regulatory element," as used herein refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

The terms "reporter gene construct," or "reporter gene vector," as used herein refers to a recombinant DNA molecule containing a sequence encoding the product of a reporter gene and appropriate nucleic acid sequences necessary for the expression of the operably linked coding sequence in a particular host organism. Eukaryotic cells are known to utilize promoters, enhancers, and termination and polyadenylation signals.

The term "reporter gene," refers to an oligonucleotide having a sequence encoding a gene product (typically an enzyme) which is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include but are not limited to bacterial genes encoding β-galactosidase (lacZ, the bacterial chloramphenicol acetyltransferase (cat) genes, firefly luciferase genes and genes encoding β-glucuronidase (GUS).

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 (1986), and Maniatis, et al., supra (1987)). For example, the SV40 early gene enhancer is very active in a wide variety of cell types from many mammalian species and has been widely used for the expression of proteins in mammalian cells (Dijkema, et al., EMBO J. 4:761 (1985)). Two other examples of promoter/enhancer elements active in a broad range of mammalian cell types are those from the human elongation factor 1α gene (Uetsuki et al., J. Biol. Chem., 264:5791 (1989); Kim et al., Gene 91:217 (1990); and Mizushima and Nagata, Nuc. Acids. Res., 18:5322 (1990)) and the long terminal repeats of the Rous sarcoma virus (Gorman et al., Proc. Natl. Acad. Sci. USA 79:6777 (1982)), and the human cytomegalovirus (Boshart et aL, Cell 41:521 (1985)).

The term "promoter/enhancer," denotes a segment of DNA which contains sequences capable of providing both promoter and enhancer functions (for example, the long terminal repeats of retroviruses contain both promoter and enhancer functions). The enhancer/promoter may be "endogenous," or "exogenous," or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals," on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York (1989), pp. 16.7-16.8). A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site," or "poly A sequence," as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamHI/BcII restriction fragment and directs both termination and polyadenylation (Sambrook, supra, at 16.6-16.7). This 237 bp fragment is contained within a 671 bp BamHI/PstI restriction fragment.

The term "genetically engineered cell line," refers to a cell line that contains heterologous DNA introduced into the cell line by means of molecular biological techniques (i.e., recombinant DNA technology).

The term "vector" as used herein, refers to a nucleotide sequence comprising at least a promoter and a gene of interest. Such a gene of interest may encode an amino acid sequence for the purpose of expressing the amino acid sequence (i.e., for example, a TSH receptor amino acid sequence). A vector has the capability of becoming integrated into foreign DNA to form a stable transfected cell.

The term "stable transfection," or "stably transfected," refers to the introduction and integration of foreign DNA into the genome of the transfected cell.

The term "stable transfectant," refers to a cell which has stably integrated foreign DNA into the genomic DNA.

The term "stable transfection" (or "stably transfected"), refers to the introduction and integration of foreign DNA into the genome of the transfected cell. The term "stable transfectant," refers to a cell which has stably integrated foreign DNA into the genomic DNA.

The term "RDluc" refers to an RD cell line having been stably transfected with a luciferase gene.

The term "CHOluc" refers to a CHO cell line having been stably transfected with a luciferase gene.

The term "selectable marker," as used herein refers to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any mammalian cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with tk cell lines, the CAD gene which is used in conjunction with CAD-deficient cells and the mammalian hypoxanthine-guanine phosphoribosyl transferase (hprt) gene which is used in conjunction with hprt cell lines. A review of the use of selectable markers in mammalian cell lines is provided in Sambrook et al., supra at pp. 16.9-16.15.

The terms "nucleic acid molecule encoding," "DNA sequence encoding," and "DNA encoding," refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The terms "confluent" or "confluency" as used herein in reference to an adherent cell line define a condition wherein cells throughout a culture are in contact with each other creating what appears to be a continuous sheet or "monolayer" of cells.

The terms "cytopathic effect" or "CPE" as used herein describe changes in cellular structure (i.e., a pathologic effect) resulting from external agents such viruses. Common cytopathic effects include cell destruction, syncytia (i.e., fused giant cells) formation, cell rounding vacuole formation, and formation of inclusion bodies. CPE results from actions of a virus on permissive cells that negatively affect the ability of the permissive cellular host to preform its required functions to remain viable. In in vitro cell culture systems, CPE is evident when cells, as part of a confluent monolayer, show regions of non-confluence after contact with a specimen that contains a virus. The observed microscopic effect is generally focal in nature and the foci is initiated by a single virion. However, depending upon viral load in the sample, CPE may be observed throughout the monolayer after a sufficient period of incubation. Cells demonstrating viral induced CPE usually change morphology to a rounded shape, and over a prolonged period of time can die and be released form their anchorage points in the monolayer. When many cells reach the point of focal destruction, the area is called a viral plaque, which appears as a hole in the monolayer. Cytopathic effects are readily discernable and distinguishable by those skilled in the art.

The abbreviation "ONPG," represents o-Nitrophenyl-13-D-Galactopyranoside. ONPG is a substrate for the enzyme β-galactosidase β-gal). The reaction between ONPG and (β-gal produces a yellow product which can be quantified spectrophotometrically at 405 nm.

The abbreviation "X-gal," represents the chemical compound 5-bromo-4-chloro-3-indolyl-(3-D-galactopyranoside, a substrate for the enzyme β-galactosidase. The reaction between X-gal and β-galactosidase results in the formation of a blue precipitate which is visually discernable.

The term "hybriwix," represents a product of Diagnostic Hybrids, Inc., Athens, Ohio which allows for quantification of certain viral DNA in an infected monolayer of cells by DNA hybridization. "DNA hybridization" is the annealing of two complementary DNA molecules whose base sequences match according to the rules of base pairing. DNA hybridization is used to identify or quantify an unknown or "target" DNA by hybridization to a known DNA or "probe." The probe is typically labeled with a reporter molecule such as $^{125}$I, a radioisotope which can be detected and quantified with a gamma counter.

The phrase "plaque reduction assay," or "PRA," as used herein describes a standard method used to determine efficacy of anti-viral drugs by enumerating a decrease in plaque formation in a cell monolayer exposed to a drug. A "plaque" is a defined area of "CPE." It is usually the result of infection of the cell monolayer with a single infectious virus which then replicates and spreads to adjacent cells of the monolayer. A plaque may also be referred to as a "focus of viral infection."

The term "permissive" as used herein describes the sequence of interactive events between a virus and its putative host cell. The process begins with viral adsorption to the host cell surface and ends with release of infectious virions. A cell is "permissive" if it readily permits the spread of virus to other cells. Many methods are available for the determination of the permissiveness of a given cell line, including but not limited to, plaque reduction assays, comparisons of the production and/or quantitation of viral proteins based on results obtained from gel electrophoresis, relative comparisons using hybridization analysis to analyze DNA or RNA content, etc.

The term "susceptible," as used herein describes the extent that a permissive or non-permissive host cell can adsorb and be penetrated by a virus. A cell line may be susceptible without being permissive in that it can be penetrated but not release virions. A permissive cell line however must be susceptible.

The phrase "seed on," as used herein describes the act of transferring an aqueous solution of suspended ceils into a vessel containing cells adhered to a surface, after which the vessel is stored for a sufficient period of time to allow the suspended cells or "seeds" to settle out by gravity and attach in a relatively uniform manner to the adhered cells and become integrated into the final cell monolayer as a mixture. A "mixed cell monolayer," results from the "seed on" process.

The phrase "seed in," as used herein describes the mixing of two or more aqueous solutions of suspended tissue culture cells, each cell suspension having different cellular properties, and transfer of such mixture of ceils into a vessel which is stored for a sufficient period of time to allow the suspended cells to settle out by gravity and attach in a relatively uniform manner such that the distribution of any single cell type is indicative of the relative ratio of the cells in the original mixture.

The term "starts," as used herein refers to the reporter cells which represent a primary infection of virus. The virus infects a reporter cell (a genetically engineered cell) and induces the expression of the reporter gene. A reporter cell can be non-permissive (i.e. permissiveness of the reporter cells is not required) and still produce starts.

The term "chimeric" as used herein, refers to any nucleic and/or amino acid sequence containing portions from two or more different species. A protein may be chimeric if the primary amino acid sequence contains portions from two or more different species (i.e., for example, an hTSH/rLH-R). A protein may also be chimeric if the primary amino acids sequence contains portions from two or more different proteins, whether from the same species or different species. A protein may also be chimeric if the quaternary amino acid structure contains proteins from two or more different species. Further, a nucleic acid may be chimeric if the primary nucleotide sequence contains portions from two or more different species. A nucleic acid may also be chimeric if the primary nucleotide sequence contains portions from two or more different proteins, whether from the same species or different species.

DETAILED DESCRIPTION

The present invention provides methods and compositions useful in the diagnosis and management of autoimmune diseases. In particular, the present invention provides methods and compositions for the diagnosis and management of Graves' disease. In addition, the present invention provides methods and compositions for monitoring the immune status and responses of individuals. In particular, the present invention finds use in montoring the immune responses of vaccine recipients. The present invention further provides methods and compositions for accelerating and enhancing the attachment of viruses to cell surface receptors, providing increased sensitivity in assays to detect and quantitate viruses in samples.

I. Graves' Disease

Typically, the clinical picture of Graves' disease in young adults is very easily recognized. The patients are more commonly female than male, and report symptoms including, but not limited to, sweating, palpitations, nervousness, irritability, insomnia, tremor, frequent stools, and weight loss in spite of a good appetite. Physical examination usually shows mild proptosis, stare, lid lag, a smooth, diffuse, non-tender goiter, tachycardia (especially after exercise) with loud heart sounds, and often a systolic murmur or left sternal border scratch, tremor, onycholysis, and palmar erythema; often, a bruit is heard over the thyroid, and a cervical hum is almost always present. In patients with these symptoms, Graves' disease is readily recognized, and can be confirmed with laboratory tests (See, Federman, Thyroid, in Dale and Federman (eds.), Scientific American Medicine, 3:1-6, Scientific American, New York, N.Y., (1997).

Although the signs and symptoms described above can be troublesome, other symptoms of the disease can be more dangerous. One of the most disturbing symptoms is severe exophthalmos, accompanied by ophthalmoplegia, follicular conjunctivitis, chemosis, and loss of vision. Additional symptoms include, but are not limited to, dermopathy, pretibial myxedema, clubbing, and in the most severe cases, acropachy. These signs and symptoms are indicative of a representative autoimmune etiology of Graves' disease.

Despite the typical clinical picture of Graves' disease, methods are needed to confirm the diagnosis, as well as provide prognostic indicators for management and treatment. In addition, in cases where the cause of hyperthyroidism is unclear, diagnostic test methods must be utilized to determine the etiology. Although in vivo methods such as radioactive-iodine uptake (RAIU) may be used in the diagnosis and monitoring of patients with Graves' disease (See e.g., Baldet et al., Acta Endocrinol. (Copenh) 116:7-12 (1987)), there are two basic groups of in vitro assay systems developed for this purpose. One is dependent upon the measurement of some index of thyroid stimulation (e.g., cAMP generation) and the other assesses the ability of thyroid-stimulating autoantibodies (TSAb) to inhibit the binding of radiolabelled thyroid stimulating hormone (TSH) to its receptor. These methods include bioassays and in vitro assays for TSAb. However, no widespread application of methods to measure the thyroid-stimulating immunoglobulin (TSI or TSAb) in Graves' disease diagnosis has been reported. (See e.g., Rapoport et al., J. Clin. Endocrinol. Metabol., 58:332-338 (1984)). In addition, it was recognized that in the sera of Graves' disease patients there is a heterogenous population of immunoglobulin G (IgG) molecules that recognize the thyroid hormone receptor (See e.g., Yokoyama et al., J. Clin. Endocrinol. Metabol., 64:215-218 1987)). Further, the recognition that TSH-binding inhibition assays do not necessarily reflect a thyroid-stimulating activity contributed to confusion in attempts to reach agreement on the clinical application of such assays (See e.g., McKenzie and Zakarija, J. Clin. Endocrinol. Metabol., 69:1093-1096 (1989)). Limitations in terms of sensitivity and specificity were also problematic. Indeed, problems associated with available assay systems resulted in arguments that the measurement of thyroid peroxidase antibodies is a sufficiently sensitive marker for underlying thyroid autoimmunity (See, Botero and Brown, supra).

As indicated by Rapoport et al., the available assays that could be performed easily, in a standardized manner, and for large numbers of samples had significant limitations in terms of sensitivity and/or specificity, making these tests unreliable for clinical use. These problems apply primarily to assays that measure the ability of TSI to inhibit the binding of radiolabelled TSH to human thyroid plasma membranes (i.e., the assays do not measure TSI activity per se). Also, not all of the anti-TSH receptor antibodies are stimulatory. Rapoport et al. further indicate that assays using TSI stimulation of adenylate cyclase activity in human thyroid plasma membranes are seriously lacking in sensitivity. Some assays are unpractical for general clinical use, including those that rely upon the use of fresh human thyroid tissue, involve extremely difficult techniques with limited sample capacity, and are very laborious and/or uneconomical (See e.g., Rapoport et al, supra).

The development of assays using cultured canine and porcine thyroid cells to measure the cAMP response to TSH were later adapted for use with human thyroid cells which offered potentially superior results. In addition to the requirement for fresh thyroid cells in some of these methods (e.g., the methods discussed by Rapoport et al.), many also required tedious and time-consuming sample preparation prior to assaying the specimens. For example, some protocols require laborious and time-consuming dialysis methods and/or precipitation of immunoglobulins in the test sera with ammonium sulfate or polyethylene glycol (See e.g., Rapoport et al., supra; and Kasagi et al., J. Clin. Endocrinol. Metabol., 62:855-862 (1986)).

In view of the problems encountered with these assay systems, other methods were investigated in an effort to develop an assay that is easy to perform, reliable, sensitive, and specific for Graves' disease autoantibodies. For example, the use of bioassays to measure cAMP production rely upon the use of cells of non-human origin grown in continuous culture or on human cells used as primary cultures or frozen in aliquots for use as needed. Problems with the use of human thyroid cells include the variability in responsiveness of surgically obtained thyroid tissue. Thus, cells of nonhuman origin gained popularity, including the rat thyroid cell line (FRTL-5). This is a non-transformed, differentiated cell line that has been well-studied and characterized (See e.g., Bidey et al., J. Endocrinol., 105:7-15 (1985); and Michelangeli et al., Clin. Endocrinol., 40:645-652 (1994)). However, a number of disadvantages make these cells less than ideal for Graves' disease assays. For example, the cells are slow growing and have fastidious growth requirements which include the need for TSH. Consequently, it is necessary to deprive the cells of TSH for at least 5 days prior to assay in order to achieve a reasonable level of sensitivity.

Subsequent development of cells such as the JP09 cells (Chinese hamster ovary cells transfected with a functional human TSH receptor) and other cell lines which stably express the human TSH receptor have greatly improved the assay systems available for the detection of Graves' disease autoantibodies. These cells have a TSH receptor that is comparable to that of native thyrocytes and possess a functional signal transduction system involving G-protein coupling, activation of adenylate cyclase and cAMP generation in response to TSH and to thyroid-stimulating antibodies (TSAb) (See e.g., Michelangeli et al., supra). These cells have been reported to be superior to FRTL-5 cells as they provide similar diagnostic information, but are more sensitive, grow faster, have less fastidious growth requirements, and respond to unextracted sera, in comparison with FRTL-5 cells (Michelangeli et al., supra; see also, Kakinuma et al., J. Clin. Endocrinol. Metabol., 82:212902134 (1997)). In addition, these methods are more rapid and reproducible, and perhaps more specific for detection of human autoantibodies directed against the human receptor. Further, the assays are easier and less cumbersome to perform than those using the FRTL-5 cell line (See e.g., Vitti et al., J. Clin. Endocrinol. Metabol., 76:499-503 (1993)). However, these assays rely upon the use of radioactivity (e.g., in radioimmunoassays) to detect and quantitate cAMP and are as a result, still cumbersome.

II. Diagnosis of Graves Disease

Thyroid-stimulating autoantibodies (TSAb) directed against the thyroid stimulating hormone (TSH) receptor are capable of stimulating thyroid adenylyl cyclase, the enzyme responsible for producing cyclic-adenosine monophosphate (cAMP). These autoantibodies have been used as diagnostic markers for detection and identification of patients suffering from Graves' disease, as these autoantibodies appear to be responsible for the hyperthyroidism seen in patients with this disease.

However, as discussed in more detail below, the methods commonly used to detect and measure these TSAbs are complex and time-consuming. One method utilizes a rat thyroid cell line known as "FRTL-5." This cell line, available from Interthyroid Research Foundation (Baltimore, Md.) expresses receptors that cross-react with human TSAbs. In the presence of TSAbs (i.e., for example, upon exposure of the cells to serum from a Graves' patient containing these antibodies), FRTL-5 cells are stimulated to produce cAMP. This cAMP is then measured in a portion of the lysed cells or the medium bathing the cells using a radioimmunoassay method. The FRTL-5 cells formed the basis for the first successful bioassay for the autoantibodies that are pathognomonic of Graves' disease. U.S. Pat. No. 4,609,622 (herein incorporated by reference).

A typical assay using FRTL-5 cells performed as described by Vitti et al. (Vitti et al., J. Clin. Endocrinol. Metabol., 76:499 (1993)) involves seeding FRTL-5 cells in 96-well plates (30,000 cells/well) in a special complete medium containing 6 hormones (i.e., for example, a 6H medium) in addition to the normal growth constituents used in cell culture medium. After 2-3 days incubation in a 5% $CO_2$, humidified, 37° C. incubator (i.e., when the cells are confluent), the medium is changed to a "Starvation Medium," which is deficient in TSH (thereby resulting in a 5H medium), wherein TSH is one of the 6 hormones in the 6H medium. The cells are then maintained for 4-5 days in the incubator with a medium change every 2-3 days. During this time the cells do not grow or multiply. Subsequently, the cells may be use in a diagnostic assay.

Early diagnostic methods for Graves' disease were performed by removing the Starvation Medium and adding a special low sodium chloride, high sucrose buffer (HBSS NaCl+222 mM sucrose; the formula for this buffer is: 0.0608 g/L $KH_2PO_4$, 0.144 g/L $CaCl_2$, 0.373 g/L KCl, 0.048 g/L $MgSO_4$, 0.097 g/L $Na_2PHO_4$, 1.0 g/L D-glucose, 76 g/L (i.e., 222 mM) sucrose, 4.77 g/L HEPES, and 10 g/L BSA; pH 7.2-7.4) containing a phosphodiesterase inhibitor (e.g., 0.5 mM methylisobutylxanthine; IBMX), to prevent this enzyme from breaking down cAMP. Specially prepared samples of patient immunoglobulin (IgG), controls, and standards are added to the appropriate wells, usually in triplicate, and the plate is incubated in a 5% $CO_2$, humidified, 37° C. incubator for 2 hours. Following this incubation, 5-10 μl of the medium are removed from each well and used in a radioimmunoassay system to detect the presence of cAMP. Typically this assay is run with about 6 standards in duplicate, with patient and controls also run in duplicate. The assay usually requires an overnight incubation with about an hour required the next day for the separation of free, radiolabelled cAMP from antibody-bound, radiolabelled cAMP.

As the use of radioactivity and long preparation times are negative aspects of the FRTL-5 assay, improved systems have been developed. One investigation involved the use of low salt conditions to increase the sensitivity of the assay system (See, Kosugi et al., Endocrinol., 125:410-417 (1989)). Additional improvements in the bioassay involved a strain of Chinese Hamster Ovary ("CHO") cells transfected with a human TSH receptor ("CHO-R"; See, Vitti et al., supra). This cell line offered two major improvements over the FRTL assay. First, this method involves the use of human TSH receptors instead of rat TSH receptors which should provide greater specificity and perhaps sensitivity for the detection of TSAbs.

Second, there is no requirement for the special 6H medium and 5H medium changes over a 6-8 day period, since the CHO-R cells grow well on a standard supplemented medium and can be used 1-3 days after seeding, depending on the density of the cell suspension used to inoculate the wells. In addition, comparative studies with FRTL-5 cells have shown that the CHO-R cells may be more accurate in detecting Graves' TSAbs (See, Vitti et al.).

A further improvement was provided by the use of CHO-R cells designed to readily assess the increased amounts of cAMP caused by TSI through the use of a reporter gene (i.e., for example, luciferase) (Evans et al., J. Clin. Endocrinol. Metabol., 84:374 (1999)). Thus, with the introduction of this engineered cell line (i.e., CHO-Rluc), the complexity and dangers inherent in the use of radioactive compounds used in the previously developed radioimmunoassay for cAMP detection and quantitation are eliminated. With these cells, luciferase is measured simply by removing the medium from the cells, adding a lysis buffer, allowing 20-30 minutes for lysis to occur, removing a sample of the lysate, adding luciferase substrate and measuring light output over a 15 second interval using a luminometer. However, as indicated in the Experimental section below, this method provides equivocal results and required further improvement.

In one embodiment, the present invention contemplates methods that incorporate the advantages of a CHO-Rluc protocol, while providing additional advantages in terms of reliability and reproducibility. Considerable development effort was dedicated to the development of methods of the present invention, including those that allow the use of CHO-Rluc cells in luminometric assays using TSH and immunoglobulins from untreated Graves' disease patients. The standard protocol originally used involved planting the CHORluc cells from a frozen stock, so as to seed at a concentration that produced confluent monolayers after 18-24 hours of incubation. Initially, the Growth Medium was removed and Stimulation Medium was added to the monolayers, to which a series of TSH standards (e.g., 0, 10, 100, 1000 μIU TSH/ml), and patient IgG samples were added. As this approach yielded poor results, an overnight starvation or conditioning period was tested. Addition of this step resulted in improved results with lower background values and appeared to be important in producing good values for the TSH standards and the test patient samples. An additional experimental option was also tested in which polyethylene glycol (PEG) was used to enhance antigen and antibody binding. In these experiments, PEG was added to the Stimulation Medium.

In various experiments, different media formulations and combinations were tested, as described in the Experimental section below. For example, starvation with the Stimulation Medium resulted in RLU/sec values of (32,103) for the 0 μIU/ml TSH standard, −1,148 for the 10 μIU TSH/ml sample, 47,478 for the 1000 μIU TSH/ml sample, and 19,350 for IgG sample #13. In this and the following discussions, the numbers in parentheses represent the 0 μIU TSH/ml value, which is subtracted from the values for the standards or samples to yield net values.

Starvation with standard HBSS resulted in RLU/sec values of (21,671) for the 0 μU/ml TSH control, 1,336 for the 10 μIU TSH/ml sample, 82,466 for the 1000 μIU TSH/ml sample, and 0.39,082 for IgG sample #13. Starvation with standard HBSS and 6% PEG in the Stimulation Medium resulted in RLU/sec values of (32,562) for the 0 μIU/ml TSH control, 5,980 for the 10 μIU TSH/ml sample, 207,831 for the 1000 μIU 5 TSH/ml sample, and 174,461 for IgG sample #13. Thus, starvation with standard HBSS yielded higher values for TSH and the Graves' disease samples, and the incorporation of PEG into the Stimulation Medium yielded even higher values. These higher values appear to impart a higher level of sensitivity in the methods of the present invention, as compared to other methods. Thus, the present invention provides improvements in ease-of-use and safety of detection methods to diagnose and monitor Graves' disease.

Graves' disease is a thyroid disorder caused by an antibody-mediated autoimmune reaction. In Graves' patients, the autoantibodies recognizing the TSHR (TRAbs) are heterogeneous, including mainly thyroid stimulating antibodies (TSAbs) and thyroid blocking antibodies (TBAbs.) TSAbs act as a TSH agonist causing hyperthyroidism while the TBAbs function as a TSH antagonist causing hypothyroidism. While TSAb and TBAb bind to different epitopes on the TSHR, TBAb binding can "neutralize" the stimulating effect of TSAb. When the TSAb binds to the TSHR, it induces the cAMP signaling pathway, TBAb does not have this effect.

Currently, several bioassays are used to diagnose Graves' disease. The Kronus® Radio Receptor Assay (RRA) kit is used for determination of TRAbs and detects both TSAbs and TBAbs but cannot distinguish between the two. Diagnostic Hybrids Inc. (DHI) previously developed a Graves' diagnostic CHO-Luc cell line that detects the TRAbs in patient serum. This cell line co-expresses the wildtype TSH receptor gene and a firefly luciferase gene which is driven by the human glycoprotein alpha subunit promoter. This wild type TSHR has epitopes that bind TSAbs and TBAbs. Binding of TBAb to the receptor can modulate TSAbs' binding, resulting in lower stimulation by the TSAbs.

In one embodiment, the present invention contemplate recombinant cell lines (i.e., for example, CHO-MC4 and RD-MC4) that express a TSH/LH/TSH chimeric receptor in combination with a firefly luciferase gene. In one embodiment, the expression is driven by a human glycoprotein alpha subunit promoter. Although it is not necessary to understand the mechanism of an invention, it is believed that by using the chimeric receptor, binding of the blocking antibodies (i.e., for example, TBAb) is either eliminated and/or reduced. In one embodiment, a chimeric receptor comprises at least one genetic modification such that only a TSAb binding region is expressed. It is believed that the recombinant cell lines have increased specificity when compared to either the CHO-Luc cells or KRONUS® assay.

III. Monitoring of Immune Response Development

As indicated above, the present invention also provides methods and compositions for the monitoring of immune response development. In particular, the present invention provides methods and compositions suitable for monitoring the response of individuals to vaccination.

In one embodiment, a pre-immune serum (i.e., serum collected prior to administration of vaccine) may be used as a baseline for control purposes. Such serum would also be collected shortly following vaccination (e.g., 1-2 weeks after vaccination), as well as periodically in the months following vaccination. The serum samples are then tested for the presence and quantity of neutralizing antibodies.

In some embodiments, diagnostic assays are conducted to monitor the response to viral antigens. In such assays, cells such as ELVIS™ (Diagnostic Hybrids, Athens, Ohio) are used in combination with a polyethylene glycol (PEG) solution of the present invention. In one embodiment, PEG enhances the antigen-antibody reaction, thereby resulting in higher reactivity.

IV. TSI Detection in CHO-MC4 and RD-MC4 Cell Lines

In one embodiment, the present invention contemplates using genetically engineered Chinese Hamster Ovary (CHO) and/or human Rhabdomyosarcoma cells (RD) for diagnosing Graves' disease and/or monitoring Graves' disease therapy.

Clinical laboratories currently utilize various cells and reaction buffer for the detection and measurement of stimulating autoantibodies specific to Graves' disease in patient sera for identifying patients suffering from this disease and monitoring their therapy. For example, cells comprising genetically modified CHO cells containing wild type human Thyroid Stimulating Hormone Receptor (TSHR) and the CRE-Luc reporter system are utilized by numerous laboratories. These cells, however, need one day for growth and one day for starvation which puts a time constraint on test results availability. On the third day, the patient's serum specimens are incubated with the cells and reaction buffer in order to detect the presence of the Graves' autoantibodies.

In one embodiment, the present invention contemplates a method for improving a thyroid stimulating immunoglobulin (TSI) detecting cell line (CHO-Luc). In one embodiment, the cell line further comprises a chimeric receptor. In one embodiment, the chimeric receptor comprising of human Thyroid Stimulating Hormone Receptor (TSHR) and rat Luteinizing Hormone (LH) (i.e., for example, Mc4).

In one embodiment, the present invention contemplates a method for expressing the Mc4 chimeric receptor in the CHO cells and/or RD cells (or other mammalian cells). In one embodiment, the method further comprises using CRE-Luc as a reporter gene to detect TSI. In one embodiment, the chimeric receptor provides greater specificity than a wild-type receptor by preferentially binding to stimulating autoantibodies (i.e., as opposed to blocking autoantibodies). In one embodiment, the chimeric receptor provides greater sensitivity than a wild-type receptor by preferentially binding to stimulating autoantibodies (i.e., as opposed to blocking autoantibodies). In one embodiment, the cell culture further comprises PEG. Although it is not necessary to understand the mechanism of an invention, it is believed that because Graves' patient sera can have both stimulating and blocking autoantibodies, the wild type TSHR receptor will bind with both antibodies equally. Further, it is believed that blocking autoantibodies can moderate and suppress stimulating autoantibody activity.

These chimeric TSH-R receptors expressed in the disclosed cell lines offer the following advantages over currently used cell lines:

1. The system results in a lower luciferase activity background leading to higher Signal:Noise (S:N) ratios.

2. The cell lines do not need to be "starved" overnight, a requirement for currently used cell lines in order to maximize the signal resulting from TSI binding. This change reduces the turn-around time from a current 3 day assay to a 2 day assay, which is very advantageous to the laboratory, the physician, and the patient.

3. The assay is designed to measure stimulating antibodies, whereas the wild type TSH-R is responsive to both stimulating and blocking antibodies whereas this Mc4 chimeric receptor is responsive only to stimulating antibodies, thereby providing greater specificity for what is being measured.

V. Chimeric TSH Receptor

In one embodiment, the present invention contemplates novel diagnostic cell lines that detect thyroid stimulating hormone receptor (TSHR) autoantibody (i.e., for example, thyroid stimulating immunoglobulin; TSI) with high detection sensitivity and specificity. In one embodiment, the cell line comprises a recombinant Chinese Hamster Ovary (CHO-K1) cell. In one embodiment, the cell line comprises a Human Rhabdomyosarcoma (RD) cell.

In one embodiment, the present invention contemplates a vector comprising a nucleic acid sequence encoding a hTSH/rLH-R linked to a firefly luciferase reporter gene and in operable combination with a glycoprotein hormone alpha subunit promoter. In one embodiment, a cell line is transfected with the vector. In one embodiment, the transfected cell line expresses a human TSHR/rat Luteinizing hormone (LH) chimeric receptor (hTSH/rLH-R), under conditions such that the luciferase reporter signal is detected.

The identity of binding sites for TSH and thyroid stimulating autoantibodies in relation to Graves' disease was initially examined by constructing human/rat chimeric TSH-R constructs. A partial substitution of the human TSH-R with the corresponding rat sequence resulted in the following chimeric receptors: i) Mc1+2 substituting amino acid residues 8-165; ii) Mc2 substituting amino acid residues 90-165; and iii) Mc4 substituting amino acid residues 261-370. The data suggested that amino acid residues 8-165 contain an epitope specific for thyroid stimulating autoantibodies which are not the same as those required by TSH. Significant heterogeneity in the binding sites between idiopathic myxedema thyroid stimulating antibodies, Graves' disease thyroid stimulating antibodies, and TSH was observed. Tahara et al., "Immunoglobulins From Graves' Disease Patients Interact With Different Sites On TSH Receptor/LH/CG Receptor Chimeras Than Either TSH Or Immunoglobulins From Idiopathic Myxedema Patients" *Biochem Biophys Res Comm* 179:70-77 (1991).

Early studies demonstrated transfection and expression of chimeric TSH receptors that included segments from rat TSH receptors and rat lutenizing hormone chorionic gonadotropin receptors. Various rat TSH amino acid sequences were substituted with the corresponding rat LH/GC sequences. The data demonstrated that amino acid residues 268-304 were not critical for generating the cAMP response but did eliminate a TSH high affinity binding site. Akamizu et al., "Chimeric Studies Of The Extracellular Domain Of The Rat Thyrotropin (TSH) Receptor: Amino Acids (268-304) In The TSH Receptor Are Involved In Ligand High Affinity Binding, But Not In TSH Receptor-Specific Signal Transduction" *Endocr J* 40:363-372 (1993). The heterogeneity of anti-TSH receptor anti-bodies was addressed by comparing binding of: i) TSH-binding inhibitory immunoglobulin; ii) thyroid-stimulating antibody; and iii) thyroid blocking antibody using a chimeric human TSH receptor wherein amino acid residues 90-165 of the human TSH receptor were substituted by equivalent amino acid residues from the lutenizing hormone chorionic gonadotropin receptor. The binding data suggest that there might be two different types of thyroid-stimulating antibodies, three different types of TSH-binding inhibitory immunoglobulins, and one nonfunctional antibody.

Chimeric TSH receptors have been reported to detect and characterize various types of circulating antibodies suspected of having a relationship with Graves' disease. Such antibodies are believed to include, but are not limited to, stimulating autoantibodies that can activate TSHR and blocking autoantibodies that can block TSHR binding by either TSH or stimulating autoantibodies. For example, chimeras of human TSHR (hTSHR) and lutenizing hormone human chorionic gonadotropin receptor (LH-hCGR) included an Mc4 chimera having amino acids 261-370 of the hTSH-R substituted with equivalent residues from a human LH/CG-R. The ability of purified IgG samples from Graves' disease sera samples to stimulate cAMP production was measured by radioimmunoassay. Kung et al., Epitope Mapping of TSH Receptor-Blocking Antibodies In Graves' Disease That Appear During Pregnancy" *J Clin Endocrinol Metab* 86:3647-3653 (2001).

The interactions between TSH stimulating and blocking autoantibodies was addressed by using two types of TSH-R chimera constructs. The first chimera is designated Mc2 having human TSH-R amino acid residues 90-165 substituted by equivalent residues from rat lutenizing hormone chorionic gonadotropin receptor. The second chimera is designated Mc1+2 having human TSH-R amino acid residues 8-165 substituted by equivalent residues from rat lutenizing hormone chorionic gonadotropin receptor. Evaluation of circulating autoantibodies in Graves' disease patients showed that blocking autoantibodies do not strongly antagonize the action of stimualting autoantibodies, but could be responsible for underestimating stimulating autoantibody activities as measured by current CHO-hTSH-R diagnostic assay methods. Kim et al., "The Prevalance And Clinical Significance Of Blocking Thyrotropin Receptor Antibodies In Untreated Hyperthyroid Graves' Disease" Thyroid 10:579-586 (2000).

The DNA sequence of the chimeric hTSH/rLH-R (Mc4) receptor contains a total of 2,324 base pairs and encodes 730 amino acids. FIG. 8. In this chimeric receptor, the human TSH-R region ranging from amino acid number 262 to 335 was substituted with the corresponding 73 amino acids from the rat luteinizing hormone (LH) receptor The sequence that drives the expression of the luciferase reporter is a 236 nucleotide glycoprotein alpha subunit promoter, which contains a cyclic AMP (cAMP) regulatory element (CRE) and was cloned by PCR. The nucleotide sequence of the cloned promoter was determined by DNA sequencing and was confirmed by sequence comparison with Gene bank sequence AF401991. An alignment of the cloned promotoer with a GPH promoter amplified by PCR from HEK cells indicate that the two sequences are identical. FIG. 9.

Figure 10:
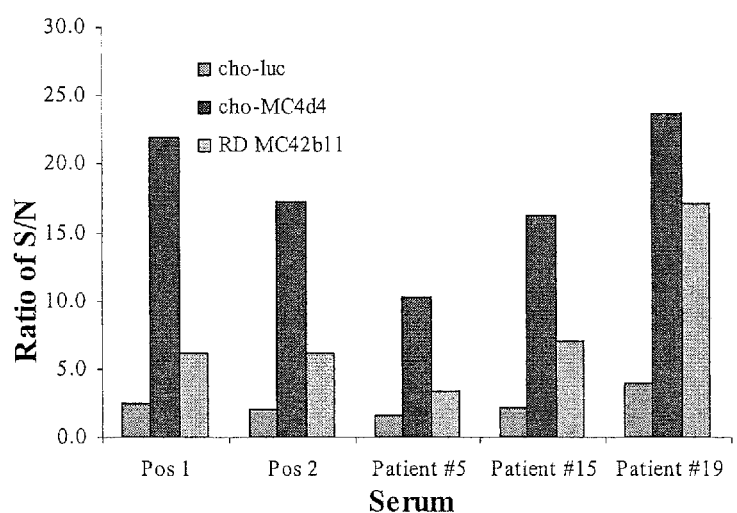
FIG. 10 presents exemplary data showing the response of the CHO-MC4, RD-MC4 and CHO-Luc cell lines to negative and positive TSI-containing sera.

The response of the CHO-MC4, RD-MC4 and CHO-Luc cell lines to negative and positive TSI sera was then compared. The cells were incubated with TSI negative and positive sera for three hours. Cells were then lysed and luciferase activity was measured by a Veritas Microplat Luminometer. The results indicated that both the CHO-MC4 and RD-MC4 cell lines had much higher detecting sensitivity when compared to the CHO-Luc cells. FIGS. 10A, 10B, 10C, 10D and 10E. A comparison of the ratio of luciferase RLU from TSI positive sera to the negative sera (ratio of S/N) shows that CHO-MC4 and RD-MC4 cells were 6-8 and 2.1-4 times more sensitive than CHO-Luc cell line. FIGS. 10B and 10D, respectively. CHO-MC4 cells were about 1.3 to 3.5 more sensitive than RD-MC4 cells. FIG. 10E. In addition, the CHO-MC4 had lower levels of induced luciferase activity than CHO-Luc when tested with TSI negative serum leading to lower background and increased signal/negative (S/N) ratios. FIG. 10A. Furthermore, both CHO-MC4 and RD-MC4 cell lines showed very low standard deviation values. FIG. 10A and FIG. 10C, respectively. A TSI positive serum, denoted #19, showed a high luciferase induction level on the CHO-MC4, RD-MC4 and CHO-Luc cell lines This serum was diluted and tested on these cell lines to compare the sensitivities. FIG. 10E.

Further, detecting sensitivity between the CHO-Luc, CHO-MC4 and RD-MC4 cell lines induced with a serially diluted TSI positive serum was compared. For example, a TSI positive serum was serially diluted and incubated on the different cell lines for three hours. The RD-MC4 and CHO-Luc cell lines showed linear responses of the ratio of S/N in the serum dilution range between 1:2 and 1:8. However, the slope of the dose response (value) and hence, the detection sensitivity, for RD-MC4 was much higher than that of CHO-Luc cell line. FIG. 11A. CHO-MC4 did not show a linear response of the ratio of S/N at no or low serum dilutions. FIG. 11B.

CHO-MC4 cells, however, did show a linear dose response of the ratio of S/N from the serum dilution ranging from 1:32 to 1:128. FIG. 11C. Note that the slope of the dose response (value) was even higher than that of RD-MC4 cell line. FIG. 11A versus FIG. 11C.

Figure 12:
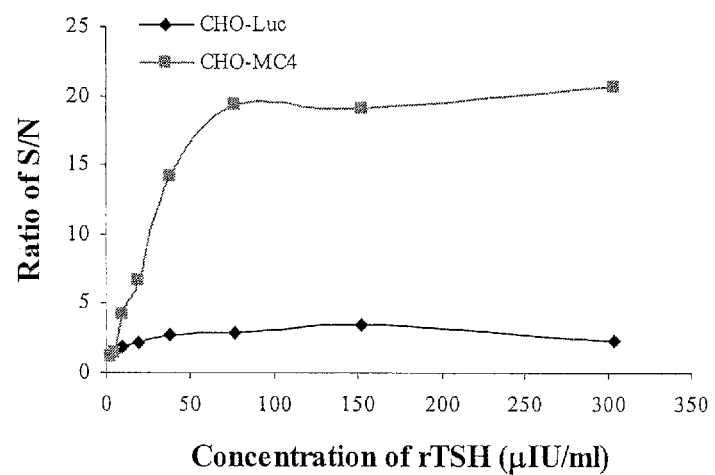
FIG. 12 presents exemplary data comparing TSH sensitivity between a CHO-MC4 cell line and a CHO-Luc cell line.

The CHO-MC4 cell line was also compared to the CHO-Luc cell line for TSH sensitivity. The S/N ratio was derived from the luciferase assay using CHO-Luc, CHO-MC4 and RD-MC4 cell lines induced with recombinant human TSH. Recombinant human TSH at various concentrations was incubated with CHO-MC4 or CHO-Luc cell lines for three hours. After incubation, the luciferase assays were performed. The results indicated that they both are able to detect TSH at a concentration as low as 50 U/ml, but the detection sensitivity of CHO-MC4 was much higher than that of the CHO-Luc cell line. FIG. 12.

Figure 13:
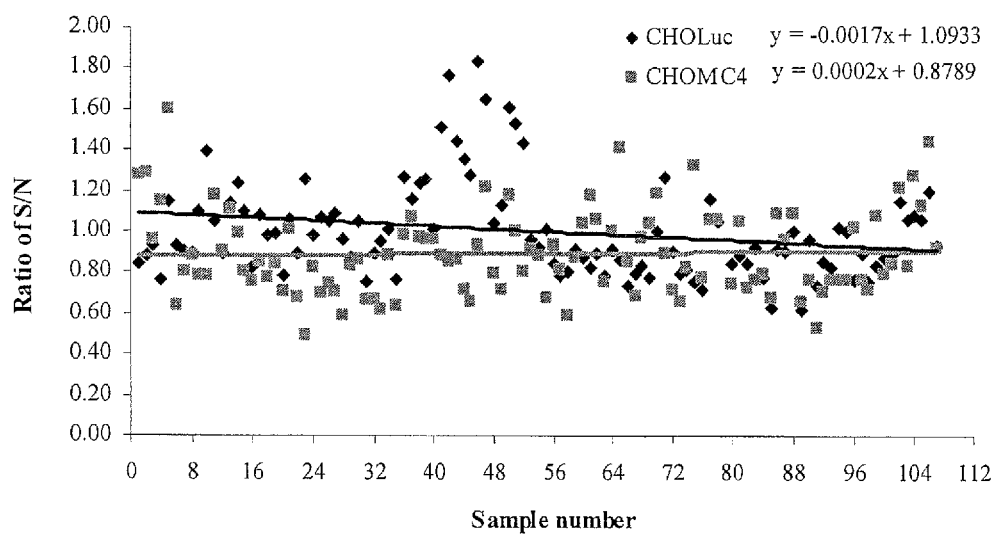
FIG. 13 presents exemplary data presenting the distribution of signal-to-noise ratios from human sera using CHO-MC4 and CHO-Luc cell lines.

CHO-MC4 and CHO-Luc cell lines were also tested for their specificity using other anterior pituitary hormones including human luteinizing hormone, (hLH) human follicle stimulating hormone (hFSH) and human chorionic gonadotropin (hCG), all of which share a common alpha subunit. Neither cell line showed any cross activity with the tested hormones. Table 1.

pattern very similar to that of the CHO-Luc cell line. The mean of the CHO-Luc cell was 1 and the CHO-MC4 was 0.88. The standard deviation of CHO-Luc was 0.23 and CHO-Luc was 0.21. FIG. 13.

Figure 14:
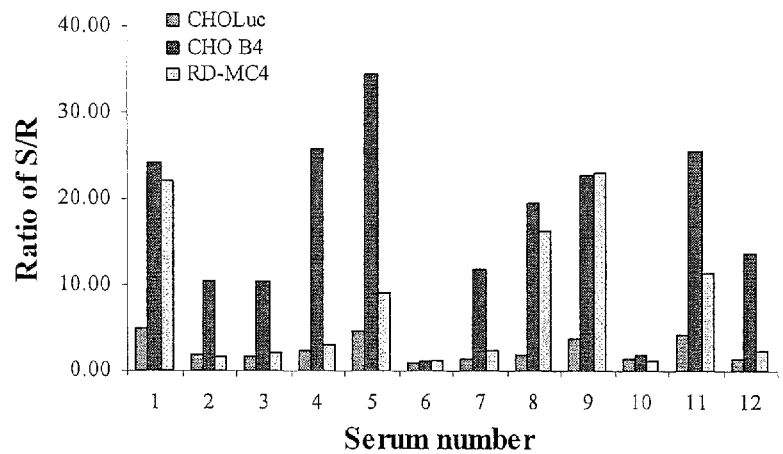
FIG. 14 presents exemplary data showing the relative sensitivity of the CHO-MC4, RD-MC4 and CHO-Luc cell lines to clinical patient serum samples.

The responses of the CHO-MC4, RD-MC4 and CHO-Luc cell lines to clinical patient serum samples were compared. The ratio of S/N derived from the luciferase assay on CHO-Luc, CHO-MC4 and RD-MC4 cell lines induced with 12 clinical serum samples. Each of the 12 serum samples was tested in the CHO-MC4, RD-MC4 and CHO-Luc cell lines. Luciferase activities of these samples were compared to that from a known negative serum sample (negative reference). The results of this study indicated that both the CHO-MC4 and RD-MC4 cell lines had much higher detection sensitivity when compared to the CHO-Luc cell line with the and CHO-MC4 cell line being the most sensitive cell line. FIG. 14.

VI. Kits

In yet other embodiments, the present invention provides kits for performing Graves' disease diagnostic assays using chimeric TSH receptors. The kits preferably include one or more containers containing a cell line-based diagnostic method of this invention. In some embodiments, the kits contain all of the components necessary or sufficient for performing a Grave's disease diagnostic assay to detect cir-

TABLE 1

Specificity of CHO-Luc and CHO-MC4 to human TSH and other hormones.

A. Luciferase S/N Comparision Of TSI Serum To Gonadotropin Hormones

| | Ratio of Signal/Negative | | | | |
|---|---|---|---|---|---|
| | Positive TSI serum | FSH (364 mIU/ml) | LH (455 mIU/ml) | HCG (29.5 IU/ml) | hTSH (76 µIU/ml) |
| CHO-MC4 | 9.4 | 0.6 | 0.9 | 0.8 | 19.4 |
| CHO-Luc | 1.9 | 0.7 | 0.8 | 0.96 | 2.9 |

B. CHO-MC4—Specific Results

| CHO-MC4 | | −TSI serum | +TSI serum | Hormones |
|---|---|---|---|---|
| FSH (36 mIU/ml) | RLU | 1589 | 15069 | 1019 |
| | Ration of S/N | | 9.5 | 0.6 |
| LH (45.5 mIU/ml) | RLU | 1737 | 15565 | 1561 |
| | Ration of S/N | | 9 | 0.9 |
| hCG (29.5 IU/ml) | RLU | 1432 | 13491 | 1168 |
| | Ration of S/N | | 9.4 | 0.8 |
| hTSH (76 µIU/ml) | RLU | 1284 | 12512 | 24880 |
| | Ration of S/N | | 9.7 | 19.4 |

C. CHO-Luc Specific Results.

| CHO-Luc | | −TSI serum | +TSI serum | Hormones |
|---|---|---|---|---|
| FSH (36 mIU/ml) | RLU | 1052 | 1929 | 728 |
| | Ration of S/N | | 1.8 | 0.7 |
| LH (45.5 mIU/ml) | RLU | 1058 | 2011 | 835 |
| | Ration of S/N | | 1.9 | 0.8 |
| hCG (29.5 IU/ml) | RLU | 946 | 1976 | 912 |
| | Ration of S/N | | 2.1 | 0.96 |
| hTSH (76 µIU/ml) | RLU | 847 | 2291 | 2495 |
| | Ration of S/N | | 2.7 | 2.9 |

CHO-MC4 and CHO-Luc cell lines were used to screen normal human sera to determine the distribution of the ratio of S/N derived from a luciferase assay. Comparisons of distribution of the S/N ratios derived from luciferase assays on CHO-Luc and CHO-MC4 cell lines induced with sera from 108 normal people were performed. All serum samples were tested in both CHO-MC4 and CHO-Luc cell lines. A known normal serum was used as a reference for calculating S/N ratios. The distribution of CHO-MC4 cell line revealed a culating TSH autoantibodies in patient sera, including all controls, directions for performing assays, and any software for analysis and presentation of results. In some embodiments, the kits contain vectors encoding chimeric TSH receptors capable of transfecting cell lines. In some embodiments, the kits comprise all materials necessary or sufficient to perform diagnostic assays in a single reaction and provide diagnostic, prognostic, or predictive information (e.g., to a researcher or a clinician). For example, such a kit might contain a cell line comprising a chimeric TSH receptor and a luciferase reporter system. In some embodiments, the kits comprise one or more of a vector comprising a first nucleic acid sequence for an Mc4 chimeric TSH receptor, a second nucleic acid sequence for a luciferin/luciferase reporter system, and a third nucleic acid sequence for a promoter. Other embodiments also include buffers, control reagents, detection devices, software, instructions, and TSH autoantibody standard preparations.

The kits may also optionally include appropriate systems (e.g. opaque containers) or stabilizers (e.g. antioxidants) to prevent degradation of the reagents by light or other adverse conditions. Each solution or composition may be contained in a vial or bottle and all vials held in close confinement in a box for commercial sale.

The kits may optionally include instructional materials containing directions (i.e., protocols) providing for the use of the reagents in the diagnosis, detection, and/or treatment of Graves' disease. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to interne sites that provide such instructional materials.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); or L (liters); ml (milliliters); µl (microliters); µIU (micro International Units); cm (centimeters); mm (millimeters); µm (micrometers); nm (nanometers); °C. (degrees Centigrade); sec. or s (second(s)); min. and m (minute(s)); MW (molecular weight); thyroid stimulating hormone or thyrotropin (TSH); bTSH (bovine TSH); TSI (thyroid stimulating immunoglobulin); TSAb (thyroid stimulating antibodies); EDTA (ethylene diamine tetraacetic acid); RLU/sec (relative light units per second); GM or PM (Growth Medium or Planting Medium); SM (Starvation Medium); HBSS (Hank's Balanced Salt Solution); EMEM (Eagle's Minimum Essential Medium); FBS or FCS (fetal bovine serum or fetal calf serum); DMSO (dimethyl sulfoxide); CHO (Chinese hamster ovary cells); CHO-R (CHO cells transfected with the human TSH receptor; CHO-Rluc (CHO-R cells transfected with the cre-luciferase reporter gene complex); Oxoid (Oxoid, Basingstoke, England); BBL (Becton Dickinson Microbiology Systems, Cockeysville, Me.)); DIFCO (Difco Laboratories, Detroit, Nil); U.S. Biochemical (U.S. Biochemical Corp., Cleveland, Ohio); Fisher (Fisher Scientific, Pittsburgh, Pa.); Sigma (Sigma Chemical Co., St. Louis, Mo.); ATCC (American Type Culture Collection, Rockville, Md.); LTI (Life Technologies, Rockville, Md.); and Promega (Promega Corp., Madison, Wis.).

In the following methods, all solutions used in these methods were sterile (with the exception of TSH, controls, patient specimens) and treated aseptically. All manipulations were conducted in a biosafety cabinet under aseptic conditions. Cell culture media (e.g., Ham's F-12, EMEM, etc.) were obtained from LTI, while additive reagents such as non-essential amino acids were obtained from Sigma.

Freezer vials of cells should not be allowed to warm from their −80° C. (or lower) storage temperature until immediately prior to thawing and use in the methods of the present invention, as cycling of the temperature may result in viability losses. Because it contains dithiothreitol, which is unstable at room temperatures, the 5× cell lysis solution should be removed from its −20° C. storage temperature only long enough to remove the required volume for preparation of the 1× solution. As it also contains dithiothreitol, reconstituted luciferase substrate solution should be kept frozen at −20° C. until just prior to use, at which time it may be removed and placed in a 25-37° C. water bath to thaw and reach room temperature.

In general, when removing liquid from wells (e.g., microtiter plates, etc.), the liquid may be dumped from the wells into a receptacle in a biosafety hood. The residual liquid can be drained and removed by placing the plate upside down on a sterile, absorbent wipe. Or, the liquid may be removed by aspiration using a fine tip on the aspirator. If aspiration is used, the plate is held at a steep angle so that the liquid does not overflow the wells, and the aspirator tip is directed down the side of the well almost to the bottom to remove the liquid and only leave minimal residue. However, care must be exercised in order to prevent disturbance of the cell monolayer, as the cells can be easily removed by the aspirator.

As indicated in the methods below, it is recommended that specimens, standards, and controls be run in triplicate. Because of the viscous nature of Solution 3 and the difficulty in achieving adequate mixing in the wells, the best reproducibility was achieved when the total triplicate volume is +10% (33 µl) of these reagents is transferred to the required triplicate volume+10% (330 µl) of Solution 3, thoroughly mixed, and 110 µl transferred to the triplicate wells.

In the preparation of cell monolayers (e.g., within the wells of microtiter plates), it is preferred that the cells be distributed evenly within the wells. Thus, in order to avoid uneven cell distributions, the transfer of cell suspensions into wells should be performed in a vibration-free biosafety hood. After all of the wells in a plate have received cells, the plate is covered and carefully placed on a solid, vibration-free surface, for 30 minutes, to allow the cells to attach undisturbed, to the bottom of the wells. This helps ensure that an even distribution of cells is present in each of the wells.

Example 1

Preparation of CHO-Rluc Cells for Testing

In these experiments, CHO-Rluc cells were prepared from W-25 CHO-R cells for use in the testing methods to detect TSI in Graves' disease patients. Pools of puromycin-resistant cells were obtained and tested for light output in response to bovine TSH. Clones with the highest light output were selected for use in the experiments described below.

CHO-Rluc cells were grown in cell culture flasks (e.g., T-225 flasks) in growth medium containing Ham's F-12 medium, 10% FBS (heated at 56° C. for 30 minutes to inactivate complement), 2 mM glutamine, and 1× non-essential amino acids. The flasks were incubated at 35-37° C., in a humidified atmosphere, containing 5% carbon dioxide.

After the cell cultures reached confluence, the medium from each flask was aspirated, and the cell monolayers were washed with HBSS without Ca and $Mg^{++}$. Then, 7 ml of a 0.25% trypsin/1 mM EDTA solution were added to each flask, and allowed to react with the monolayers for approximately 5-10 minutes at room temperature, in order to detach and disperse the cells in a nearly unicellular suspension. The cell suspensions were then centrifuged for approximately 5 minutes at 300-400×g. The supernatants were then removed and the pelleted cells resuspended in 8 ml of a medium prepared by mixing 4 ml EMEM containing 1×HBSS and 20% FBS with 4 ml of cryoprotective medium (EMEM containing 1×HBSS and 15% DMSO).

An aliquot of each cell suspension was then used to determine the number of cells present in the suspension. This determination can be accomplished using any method known in the art, including but not limited to methods using a hemocytometer to determine the cell count. Thus, it is contemplated that any method can be used to determine the cell count in the suspensions. Based on the number of cells in the suspension, the cells were aliquoted by volume to approximately $2 \times 10^6$ cells into standard freezer vials. The cells were then stored frozen at −90° C. for short-teen storage. For long-term storage, the cells were stored in liquid nitrogen (about −200° C.).

Example 2

CHO-Rluc Assay Plate Preparation and Testing

In these experiments, CHO-Rluc cells prepared as described in Example 1 were used in assays for diagnosis of Graves' disease. To prepare 24 monolayers for testing, 24 wells in a 96-well microtiter plate were first treated by adding 50-100 µl 0.1% gelatin solution (Sigma) to enhance attachment of the cells to the bottom of the 24 wells chosen for the test. Following incubation for approximately 1 minute at room temperature, the gelatin solution was removed from each of the wells by aspiration. It was noted that the gelatin can remain on the cells for longer than one minute. The gelatin serves to coat the wells with collagen, so that the cells attach more quickly to the wells and reach confluence more rapidly. However, cells can be planted and grown to confluence without gelatin and still perform well.

A freezer vial of CHO-Rluc cells produced as described in Example 1 was rapidly thawed in a 37° C. water bath to provide approximately 0.4 ml cell suspension, which was well-mixed using a pipette. The cells were then added to 2.5 ml GM (also referred to as "Planting Medium"), thoroughly mixed by vortexing for 1-2 seconds, and 100 µl aliquots of the cell suspension were added to each well, and the plates were covered. It is preferable to produce an even distribution of cells in each well. Thus, to avoid uneven cell distributions, the microtiter plate should be placed in a vibration-free hood for cell planting and attachment of cells to the walls of the microtiter plate. The planted cells were then incubated at 35-37° C., in a humidified atmosphere, containing 5% $CO_2$, for approximately 20-24 hours, to allow the cells to form a nearly or completely confluent monolayer.

The GM was then aspirated from each well as completely as possible, being careful not to disturb the monolayers (i.e., confluent monolayers remain in the wells). The monolayers were rinsed with approximately 100 µl Starvation Medium (HBSS containing $Ca^{++}$ (0.14 g/L) and $Mg^{++}$ (0.048 g/L) per well. The Starvation Medium was aspirated and a fresh 100 µl of Starvation Medium was then added to each well. It is important that these steps be conducted sufficiently rapidly that the cell monolayers do not dry. The plates were then incubated overnight in a 35-37° C., 5% $CO_2$, humidified incubator. Following incubation, the Starvation Medium was aspirated from the wells, using care to avoid disturbing the monolayers. Then, approximately 100 µl Stimulation Medium were added to each monolayer, again working quickly so that the monolayers did not dry.

Then, in an alternative method to that previously described, 10 µl of patient, control, and TSH standard solutions were added to the appropriate wells. The TSH standards and IgG samples were diluted with diluent (i.e., HBSS—NaCl+222 mM sucrose). The TSH standards were tested at concentrations of 0, 10, 100, 1000, and 5000 µIU. Patient samples were diluted to a concentration of 10 mg protein/ml for use in the assay. As the Stimulation Medium is viscous, thorough mixing of the suspensions was important. Adequacy of the mixing was ascertained by microscopic examination of the monolayers. The plates were incubated for 4 hours at 35-37° C. in a 5% $CO_2$, humidified incubator. The medium was carefully aspirated from each well and 150 µl lysis solution (Promega) was added to each well. The lysis solution contained 25 mM Tris-phosphate, pH 7.8, 2 mM diaminocyclohexane tetraacetic acid (CDTA), 2 mM dithiothreitol (DTT), 10% glycerol, and 1% Triton X-100. The plates were then incubated for 30 minutes at room temperature, to allow the monolayers to lyse. Following lysis, each well was scraped and stirred using a pipet tip. Then, 25 µl of lysate were removed from each well and placed in a luminometer tube (12×75 mm, polypropylene), and 50 µl of luciferase substrate (Promega) were then added. The tubes were vortexed for 1-2 seconds and the RLU/sec values determined, using settings of 5 seconds delay and 10 second read. To obtain average net values, the average of the "0 TSH" (i.e., the negative control) samples was subtracted from all test average values.

Example 3

Preparation of IgG Samples

In these experiments, patients' IgG was prepared for testing in the present methods. Lyophilized IgG samples from 38 well-known and characterized, untreated Graves' disease patients were kindly provided by Dr. B. Y. Cho (Department of Internal Medicine, Seoul National University, College of Medicine, Seoul, Korea). As most of the samples had been previously tested in standard methods using CHO-R and FRTL-5 cells, these test results were known for 35 of these samples.

In preparation for lyophilization, the IgGs were affinity-purified using protein A-Sepharose CL-4B columns, as known in the art, and then dialyzed against 100 volumes of distilled water at 4° C. The dialysis water was changed every 8 hours over a 2 day period. After removal of denatured protein by centrifugation at 1500×g for 15 minutes at 4° C., the IgG was lyophilized and stored at −20° C. until used in the experiments described herein.

In some experiments, purified untreated Graves' IgG was diluted in normal serum (euthyroid sera discussed in Example 7, below), and assayed using the CHORluc assay described below.

Example 4

CHO-Rluc Assays

In these experiments, the performance of CHO-Rluc cells using the method described by Evans et al. (Evans et al., J. Clin. Endocrinol. Metabol., 84:374 (1999)) was evaluated. The media from the cell monolayers in the 24 wells used in the 96-well microtiter plates prepared as described in Example 2 were aspirated and replaced with 100 µl Ham's F-12 medium containing 10% charcoal-stripped calf serum (Sigma), and incubated overnight at 35-37° C., in a humidified atmosphere containing 5% $CO_2$.

Then, 10 µl of bovine TSH standards diluted to a range of concentrations (e.g., 0 10, 100, and 1000 µIU) and Graves' IgG (dissolved to a concentration of 10 mg protein/ml in charcoal-stripped calf serum) were added to respective quadruplicate wells. The suspension in each well was mixed, and the plates were incubated for 4 hours at 35-37° C., in a humidified atmosphere containing 5% $CO_2$. The medium was then aspirated from each of the wells, and 150 µl of lysis buffer (Promega, as described above) were added to each well. The plates were then incubated at room temperature for 30 minutes to allow lysis of the cells in the wells. Then, 25 µl of each lysate were transferred to a 12×75 polyethylene luminometer tube, to which 50 µl of luciferase substrate (Promega) were added immediately prior to mixing and reading in the luminometer at settings of 5 seconds delay and 10 second read. The luminometer read out provided results as relative light units per second (RLU/sec). The negative or "zero" TSH standard value was subtracted from each of the readings. In one run, the average net value for the zero µU/ml TSI standard was 68,011 RLU/sec, while the result for the sample containing 10 µIU/µl was 4031 RLU/sec, the sample containing 1000 µIU was 222,801 RLU/sec, one Graves'IgG test sample was 384 RLUTsec (sample #1), and another Graves' IgG test sample was –3012 RLU/sec (sample #9).

The Graves' IgG sample #1 and sample #9 were previously assayed using standard FRTL-5 cells and a cAMP RIA assays. In the cAMP assay, values greater than 153 with FRTL-5 cells are considered positive for the presence of TSI. The cAMP value with FRTL-5 cells for sample #1 was 212, and the cAMP value for sample #9 was 803. The CHO-R values for these same samples (#1 and #9) were 116 and 1733, respectively, in an assay system where CHO-R values greater than 173 are considered to be positive for Graves' disease. Thus, these results clearly indicate that there is a discrepancy between the results obtained using different cell lines for the detection of Graves' disease. Indeed, the use of the Evans et al. method yielded negative results for both IgG samples, indicating that this system with CHO-Rluc is useless for detecting human TSI, despite the fact that the response to bovine TSH was very good.

Furthermore, during the development of the present invention (as described below), it was determined that if the CHO-Rluc cells were planted in a medium containing charcoal-stripped calf serum for 24 hours (i.e., to reach confluence), the cells simply attached to the bottom of the wells, but did not multiply and become confluent during the incubation period, unlike the situation in which normal FBS was used. Thus, this surprising result indicates that the use of charcoal-stripped serum in the medium resulted in a starvation step for the cells, somewhat analogous to the incubation of FRTL-5 cells in 5H medium.

In some experiments purified, untreated Graves' IgG diluted in normal serum, were tested in the CHO-Rluc assay (with PEG). For IgG #10, (2 mg/ml), the RLU/sec value was 131,461; for IgG #15 (2 mg/ml), the RLU/sec value was 180,327; for IgG #27 (5 mg/ml), the RLU/sec value was 179,777; and for IgG#32 (5 mg/ml), the RLU/sec value was 112,627. These results clearly shove that the CHO-Rluc assay measures TSI in the presence of serum.

Example 5

Development of Media Formulations

In view of the previously-described experiments, the effects of different media formulations were investigated for use with the CHO-Rluc cells in the measurement of bovine and human TSI. In these experiments, various media formulations were tested for the "starvation," and "stimulation" steps in th• CHO-Rluc assay, using bTSH standards and IgG extracted from the sera of Graves' disease patients.

In these experiments, once the cell monolayers contained within the wells of 96-well microtiter plates (as described above), reached confluence, the Growth Medium was removed by aspiration and 100 µl of Starvation Medium were added to each monolayer. The plates were then incubated for 16-24 hours at 35-37° C., in a humidified atmosphere containing 5% $CO_2$, to starve or condition the cells. The Starvation Medium was then aspirated from the wells.

To perform the assay, 10 µl of the patient specimen IgG, bTSH standards, and IgG controls (normal and Graves' disease sera), were added to the monolayers in triplicate. The suspensions were mixed within each well, and incubated under the above conditions for 4 hours. The liquid was then removed from each monolayer by aspiration, and 150 µl of lysis buffer (Promega, as described above) were added to each well. The plates were allowed to incubate at room temperature for 30 minutes to lyse the cells in the monolayers.

In order to measure the amount of cell stimulation caused by the TSH standard or antibody to the TSH receptor, the luciferase in the cell lysates was measured by adding 25 µl of lysate to a luminometer tube to which 50 µl of substrate solution (Promega) were added. The suspensions were mixed and then read in a luminometer with settings of a 5 second delay and a 10 second read, to determine the RLU for each sample.

In order to use the cells for TSI or TSH stimulation, the Starvation Medium was removed by aspiration, and 100 µl of the Stimulation Medium were added to each well. This Stimulation Medium was HBSS—NaCl+222 mM sucrose. The following Table 2 provides a comparison of the formulations of HBSS—NaCl+222 mM sucrose and standard HBSS.

TABLE 2

HBSS Medium Formulation Comparisons

| Component | HBSS- - - -NaCl + 222 mM Sucrose (g/L) | Standard HBSS (g/L) |
|---|---|---|
| $CaCl_2$ | 0.144 g/L | 0.14 g/L |
| KCl | 0.373 | 0.400 |
| $KH_2PO_4$ | 0.060 | 0.060 |
| $MgSO_4$ | 0.048 | 0.048 |
| $Na_2HPO_4$ | 0.097 | 0.048 |
| $NaHCO_3$ | 0.00 | 0.35 |
| NaCl | 0.00 | 8.00 |
| D-Glucose | 1.00 | 1.00 |
| Sucrose | 76.00 | 0.00 |
| HEPES | 4.77 | 0.00 |
| Bovine Serum Albumin | 10.00 | 0.00 |

This Stimulation Medium formulation is a formulation that is commonly used in the measurement of TSI in FRTL-5 and CHO-R cells.

The results of experiments to test various Starvation Medium formulations are indicated in the following Table 3. In these experiments, the HBSS—NaCl+222 mM sucrose Stimulation Medium was used. As indicated in Table 3, the standard HBSS with 20 mM sucrose yielded the best signal to noise ratio (i.e., the lowest background and highest value for Graves' IgG).]

TABLE 3

RLU/Sec Results for Various Starvation Media

| Starvation Medium | 0 TSH | 10 µIU TSH/ml | 1000 µIU TSH/ml | #13 IgG |
|---|---|---|---|---|
| CHO GM* | (66,232) | 782 | 265,195 | 5,144 |
| CHO Char** | (50,638) | 5,602 | 229,492 | 34,042 |
| HBSS- - - -NaCl + 222 mM Sucrose | (32,289) | 2,188 | 142,666 | 30,640 |
| Standard HBSS with 20 mM Sucrose | (27,139) | 14,390 | 156,548 | 53,994 |

*CHO GM is CHO Growth Medium containing 10% FBS.
**CHO Char. is CHO Growth Medium with 10% charcoal-stripped calf serum.

Example 6

Use of PEG

As PEG may be used in in vitro antigen/antibody reactions to assist or enhance the reaction rate, a trial was conducted in which PEG was incorporated into the Stimulation Medium. As this compound may decrease the off-rate or dissociation of the antigen/antibody complex, the use of PEG in the methods of the present invention was investigated.

Preliminary results with 12% PEG-8000 (i.e., ave. MW 8,000) in HBSS—NaCl sucrose, resulted in monolayers with increased spaces between the cells. To reduce this apparent osmotic stress, 6% PEG-8000 in HBSS—NaCl+111 mM sucrose was tested. In these experiments, the Starvation Medium yielding the best results (i.e., standard HBSS+20 mM sucrose) was used. The results are shown in Table 4, below.

TABLE 4

RLU/Sec Results for Stimulation Media With and Without PEG

| Stimulation Medium | 0 TSH | 10 µIU TSH/ml | 1000 µIU TSH/ml | #13 IgG |
|---|---|---|---|---|
| HBSS- - - -NaCl + 222 mM Sucrose | (21,671) | 1,336 | 82,466 | 39,082 |
| HBSS- - - -NaCl + 111 mM Sucrose + 6% PEG-8000 | (32,562) | 5,980 | 207,831 | 174,461 |

As indicated in Table 4, the incorporation of 6% PEG-8000 significantly and substantially enhanced the luminescent signal from the CHO-Rluc cells, in response to added bTSH, as well as Graves' IgG.

An additional experiment was conducted to determine the optimal concentration of PEG-8000 to use in the Stimulation Medium. The net values for one Graves' sample (Graves' IgG #20), with an FRTL-5 cAMP value of 957, are shown in Table 5. As indicated in Table 5, 6% PEG yielded maximum signal for Graves' TSAb.

TABLE 5

RLU/Sec Results for Various PEG Concentrations

| | % PEG In Stimulation Medium | | | | |
|---|---|---|---|---|---|
| Results | 2% | 4% | 6% | 8% | 10% |
| RLU/sec | 15,566 | 52,259 | 87,908 | 73,260 | 47,991 |

Subsequent experiments have shown that the Starvation Medium need not contain 20 mM sucrose, as there is no statistically significant difference in the results with or without it.

In addition, experiments were conducted to demonstrate that the assay of the present invention measures thyroid-stimulating immunoglobulin in a dose-dependent manner. In these experiments, three Graves' disease IgG samples (#6, #11, and #16) were tested. Serial 3-fold dilutions were made using the Stimulation Medium containing 6% PEG-8000, and the methods described above. The results are shown in FIG. 1, which shows the linearity of the dilutions. The IgG samples were prepared from 10 mg/ml stocks, which were then tested undiluted, and serially diluted (3-fold dilutions) to 0.3333, 0.1111, 0.0371, 0.0123, and 0.0041 dilutions (i.e., to yield 3.333 mg/ml, which was then diluted 3-fold to yield 1.111 mg/ml, etc.).

The FRTL-5 value for IgG sample #6 was 2080, while the FRTL-5 value for IgG sample #11 was 4453, and for IgG sample #16, the value was 830. The following Table 6 lists the results for each of these samples. The correlation coefficients (r) were 0.857 for IgG sample #6, 0.858 for sample #11, and 0.995 for sample #16.

TABLE 6

Dose-Response (Dilution) Curves of Graves' IgG Specimens*

| | Dilution Factor | | | | | |
|---|---|---|---|---|---|---|
| Sample | 1 | 0.3333 | 0.1111 | 0.0371 | 0.0123 | 0.0041 |
| IgG #6 | 176,123 | 159,694 | 62,115 | 13,480 | −6,628 | −2,574 |
| IgG #11 | Not Done | 368,373 | 324,143 | 158,641 | 77,298 | 30,166 |
| IgG #16 | 222,413 | 90,646 | 40,048 | 8,093 | −1,705 | −691 |

*All values are reported as RLU/sec.

Example 7

Alternative Protocol Using PEG

In these experiments, alternative protocols using PEG were tested. First, freezer vials of CHO-RLuc cells were thawed, diluted in Growth Medium (the contents of each cell vial were added to 2.5 ml medium), and 100 µl of this cell suspension were added to each of the 24 gelatin-coated wells of a 96-well microtiter plate, prepared as described previously. The plates were incubated for 20-24 hours in a 35-37° C., humidified incubator with an atmosphere containing 5% $CO_2$. This provided monolayers that were loosely confluent.

The Growth Medium was removed and the monolayers rinsed with 100 µl of Starvation Medium (normal HBSS with $Ca^{++}$ and $Mg^{++}$), and a final 100 µl were added to each monolayer before incubating overnight under the conditions described above. Following incubation, the Starvation Medium was removed and 100 µl of Stimulation Medium containing 6% PEG (i.e., as described above) were added to each monolayer. Then, 10 µl of each of the standards and samples were placed into the wells (in triplicate). While other volumes were tested (e.g., 25 μl, 50 μl, and 75 μl), the values obtained were substantially equivalent to those obtained with 10 μl volumes. Thus, the smaller volume was used in order to conserve the samples and reagents, and to minimize the concentration of potentially interfering substances present in some serum samples.

The well contents were mixed and the monolayers incubated as described above for 4 hours (i.e., a stimulation step). The medium was removed from each well, and 150 lal of lysis solution (as described above) were added to each well. The monolayers were allowed to stand at room temperature for 30 minutes for lysis to occur. Then, 25 μl of each lysate were added to individual luminometer tubes. Fifty microliters of luciferase substrate (as described above) were added to each tube, the contents mixed, and the tubes immediately read in a luminometer with settings of 5 seconds delay and a 10 second read time.

Figure 7:
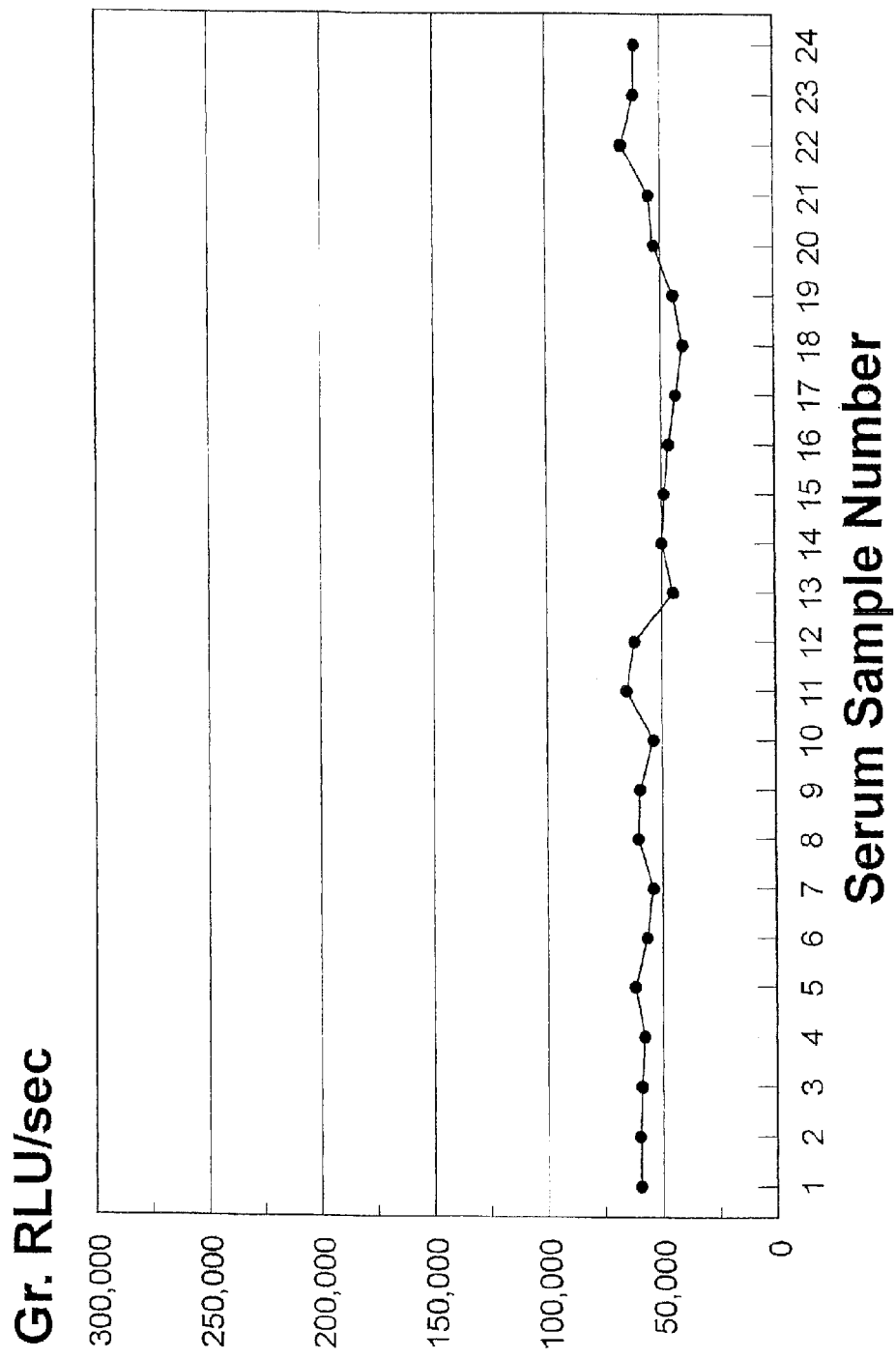
FIG. 7 shows the results for a group of normal samples (10 μl of AML "normal" specimens).

In an experiment to determine the normal range of euthyroid sera, 24 specimens obtained from a reference laboratory were run using the CHO-Rluc assay as described above. The sera were euthyroid in that none of the samples were submitted for thyroid testing. The mean (55,334 RLU/sec) and standard deviation (1 SD 7,434 RLU/sec) were calculated for these 24 euthyroid samples. The results are shown in FIG. 7. The SD value was then multiplied by three, which yielded a cut-off value for normal, non-Graves' disease values of 77,636 RLU/sec. This cut-off encompasses >99% of the normal population; values greater than this were considered to be TSI positive.

In a separate set of experiments, a group of 17 patient specimens which previously been tested by a commercial esoteric testing laboratory using cAMP RIA and FRTL-5 cells for TSI, were tested using the CHO-Rluc cells with the above procedure. The FRTL-5 test results indicated 16 of the patient specimens were negative for TSI (i.e., only one was positive). The single positive specimen identified by the FRTL-5/cAMP assay (258% or 1.98× the cut-off, where the assay cut-off was 130%), was likewise positive by the CHO-Rluc assay (190,691 RLU/sec) based on a 2.45× cut-off of 77,636 RLU/sec, as shown in FIG. 7. The CHO-Rluc values of the 16 patient specimens which were negative (i.e., normal) by the FRTL-5/cAMP assay were found to be in good agreement with the 24 normal sera used to establish the normal range for the assay. See, FIG. 7.

Example 8

Comparison of RHO-Rluc Method and Standard Methods

Figure 4:
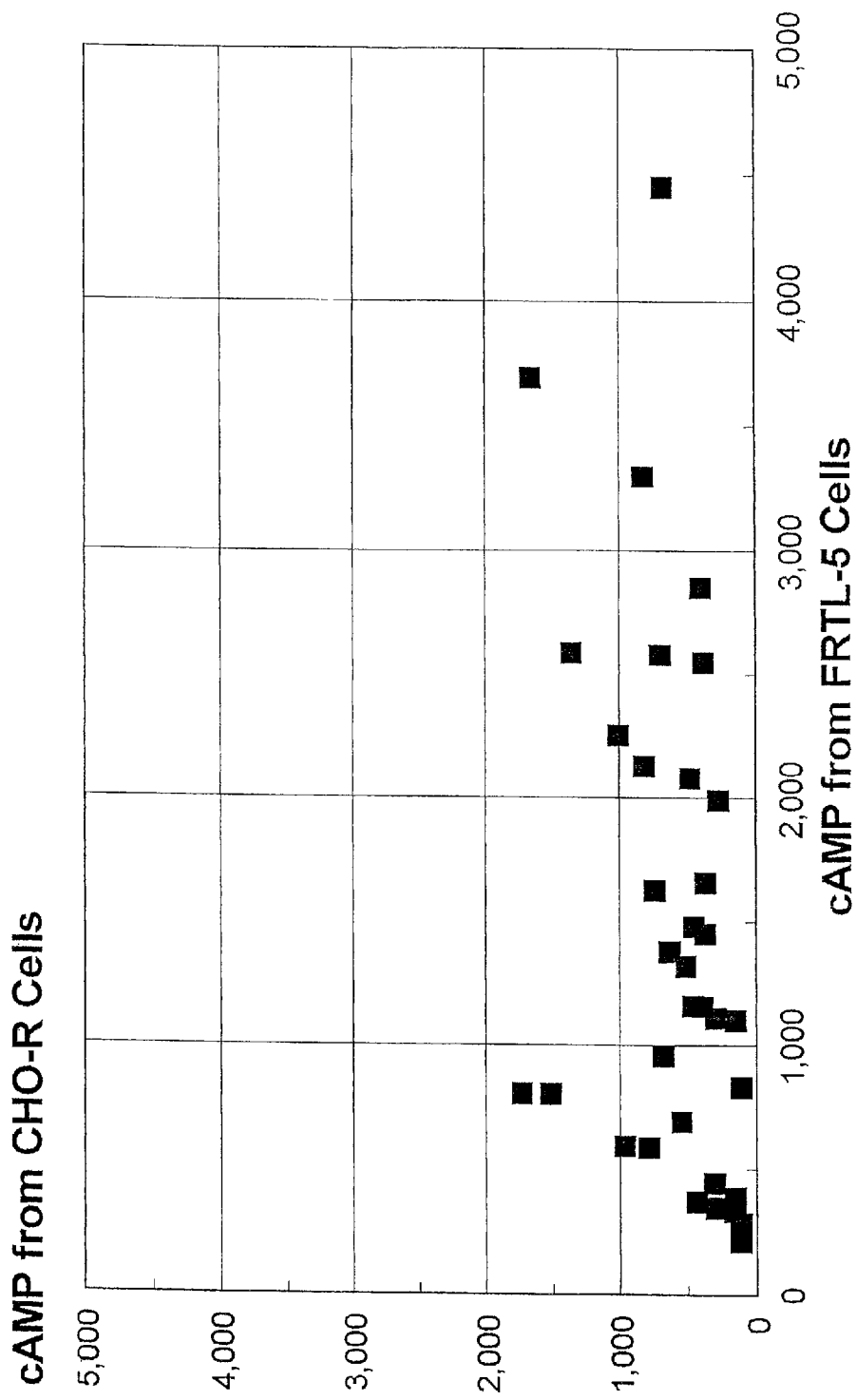
FIG. 4 provides a comparison of CHO-R cAMP results with FRTL-5 cAMP results for IgGs from 35 untreated Graves' patients.
Figure 5:
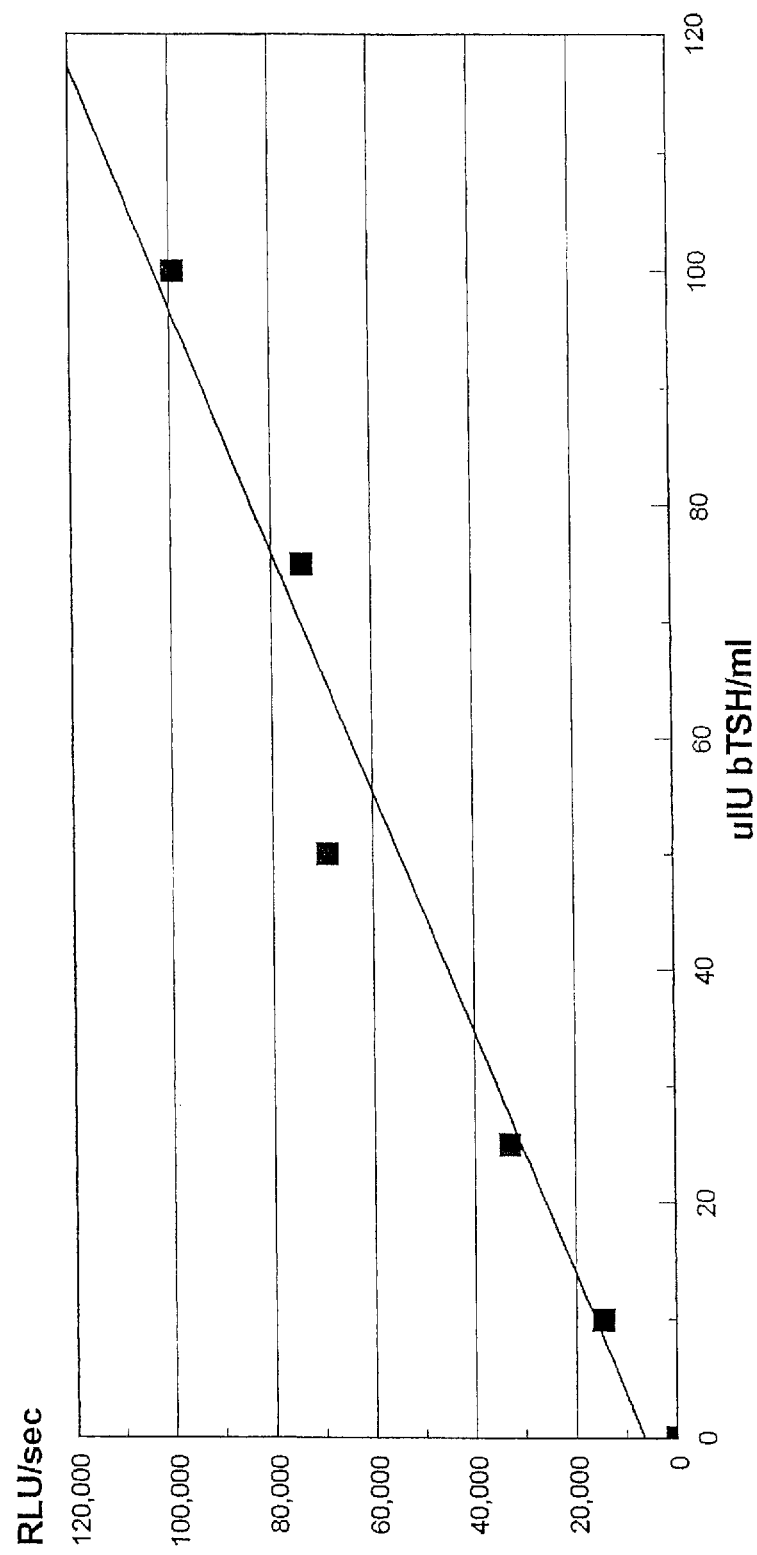
FIG. 5 shows the linearity of the response to bTSH of the CHO-Rluc cells.
Figure 6:
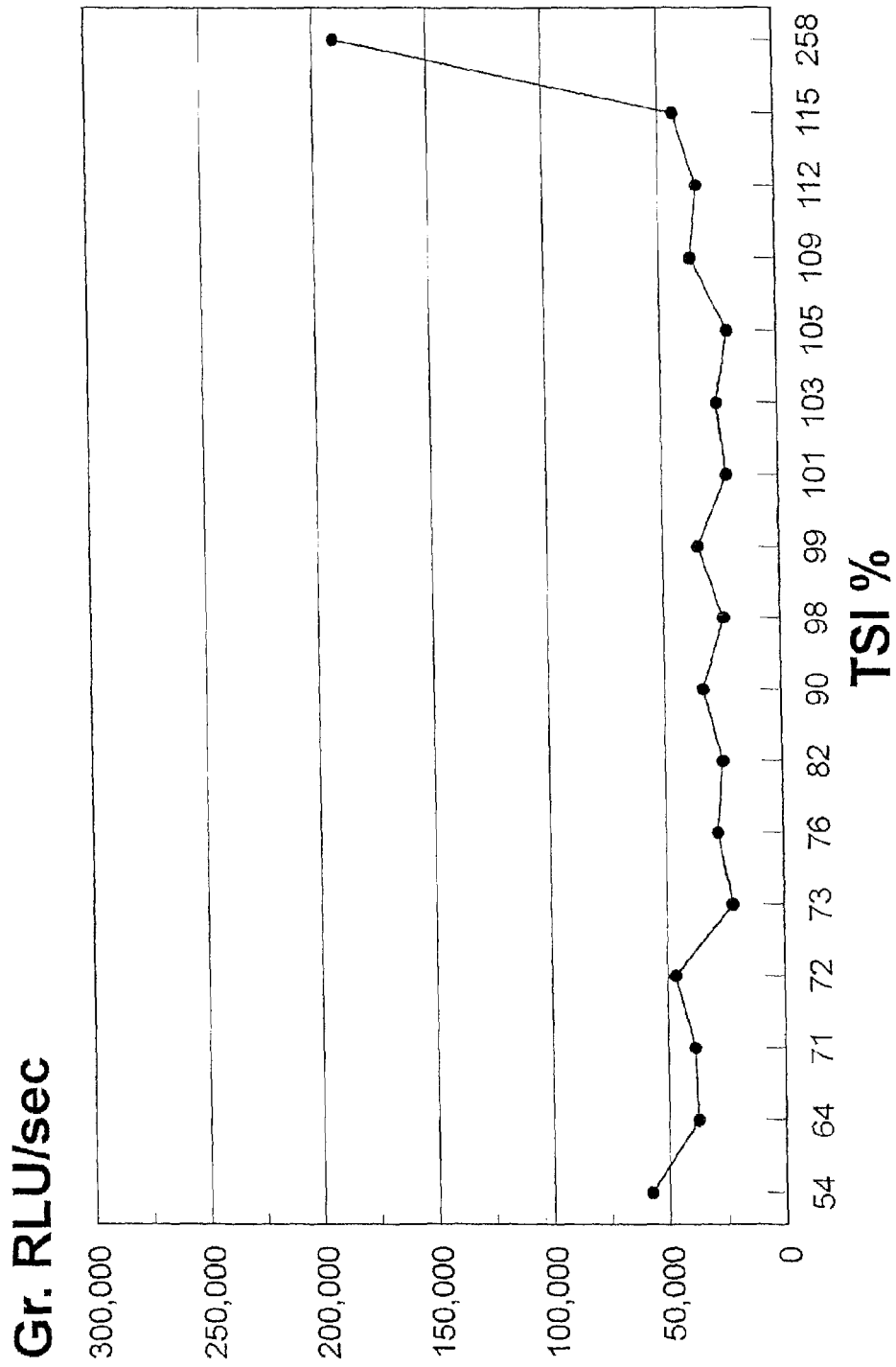
FIG. 6 shows the results for a group of samples with known TSI results using FRTL-5 cells (10 p.1 samples of LCA TSI specimens).

In these experiments, the methods of the present invention utilizing Stimulation Medium containing 6% PEG-8000 were compared with methods using the standard HBSS-containing Starvation Medium and Stimulation Medium, to obtain luciferase values for 35 of the untreated Graves' disease IgG specimens obtained from Dr. Cho. The cAMP values obtained by Dr. Cho with FRTL-5 and CHO-R cells using the same IgG samples as used in methods of the present invention are shown in comparison with the CHO-R luciferase results in FIGS. 2, 3 and 4. FIG. 5 shows the linearity of luciferase response to bTSH.

Figure 2:
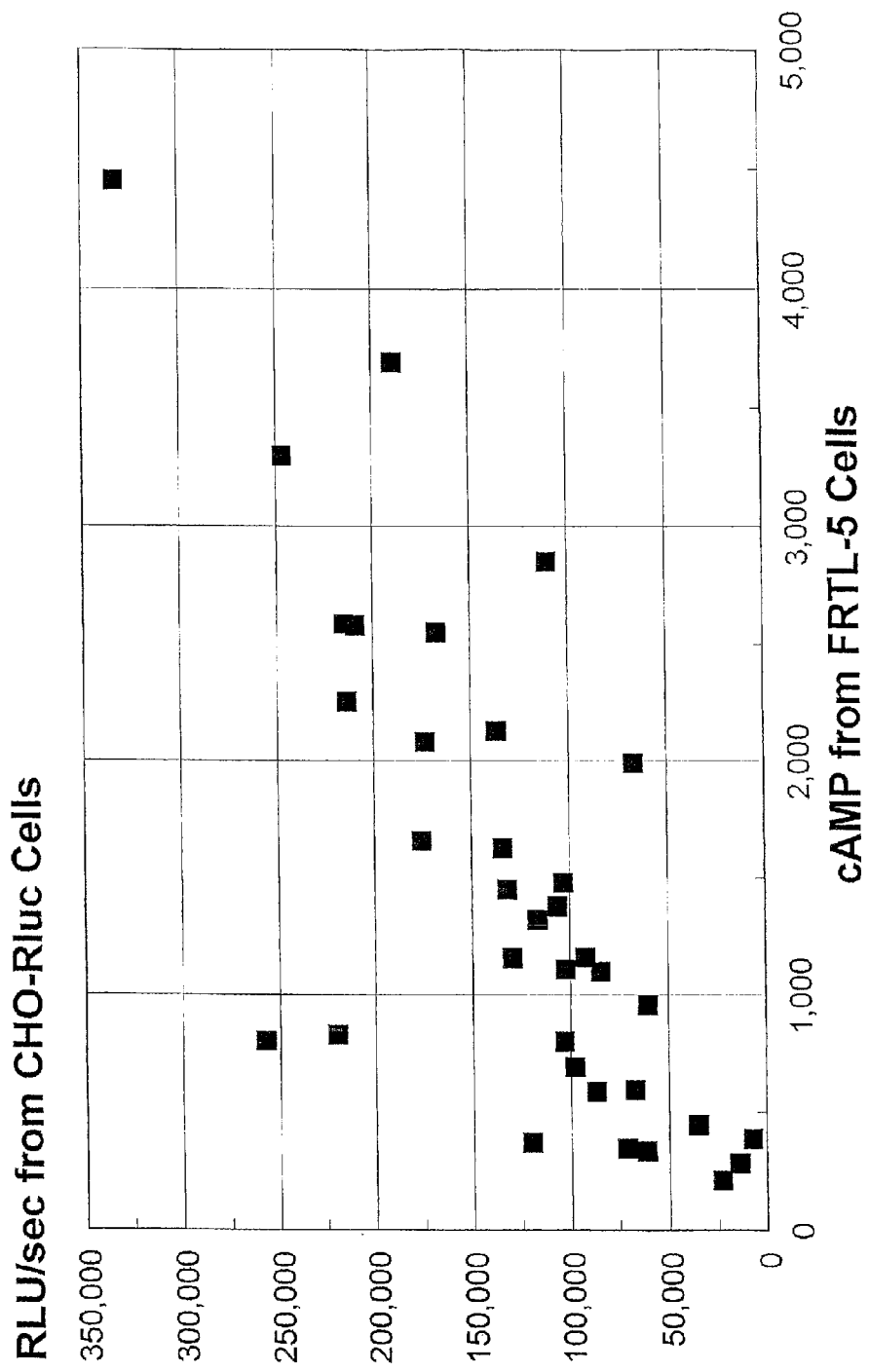
FIG. 2 provides a comparison of CHO-Rluc luciferase results with the FRTL-5 cAMP results for IgGs from 35 untreated Graves' patients.
Figure 3:
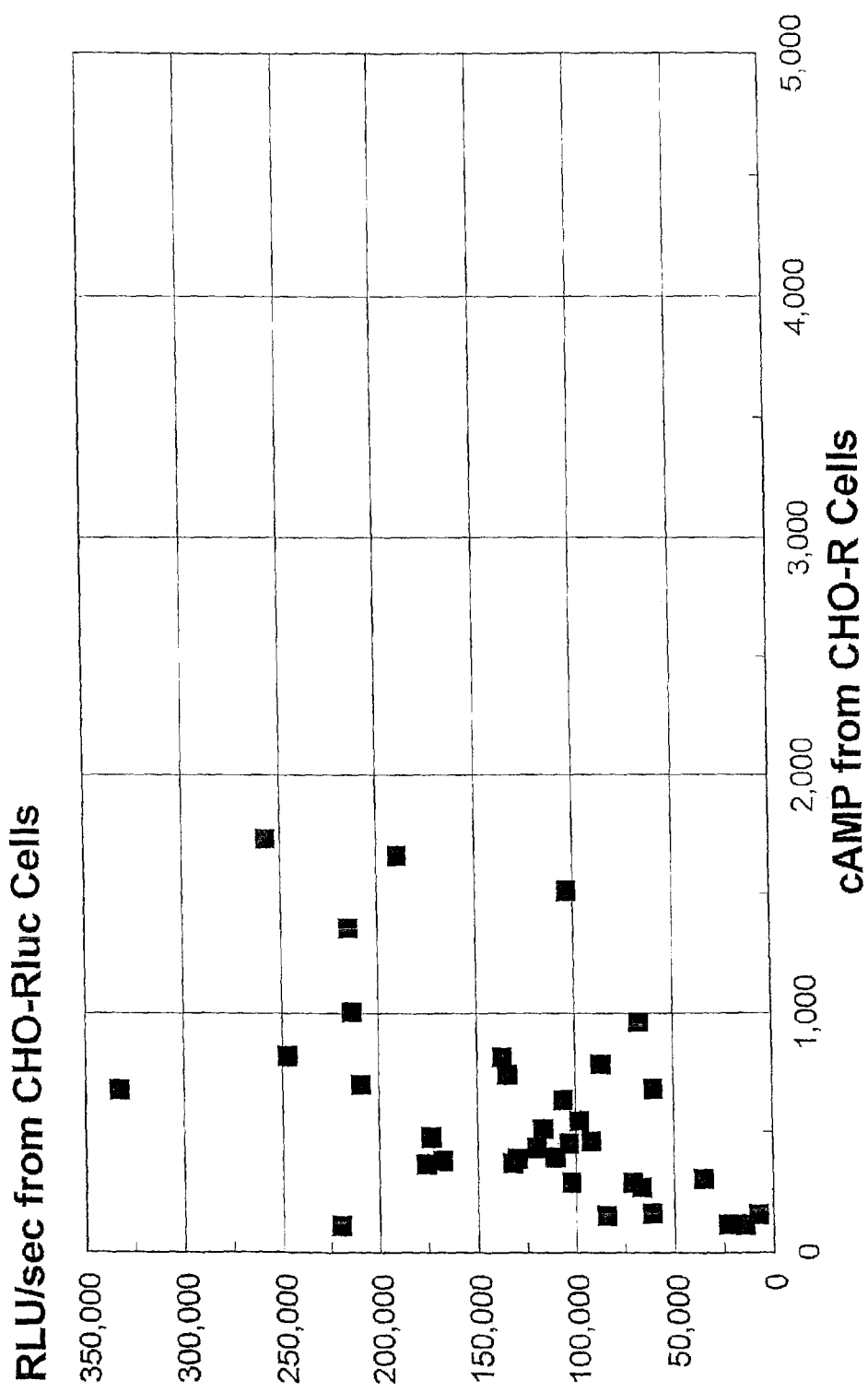
FIG. 3 provides a comparison of CHO-Rluc luciferase results with CHO-R cAMP results for IgGs from 35 untreated Graves' patients.

FIG. 2 provides a comparison of CHO-Rluc luciferase results with the FRTL-5 cAMP results. This Figure indicates that the correlation between these methods is quite good. FIG. 3 provides a comparison of CHO-Rluc luciferase results with CHO-R cAMP results. The CHO-R CAMP cut-off value was 173. Values below this cutoff were as follows (CHOluc RLU/sec): 110 (219,913), 113 (14,434), 116 (25,373), 152 (84,493), 156 (7576), and 161 (61,321). As indicated in this Figure, the range of CHO-R cAMP results is relatively narrow, as compared with the CHO-Rluc values. This is also shown in FIG. 4, which provides a comparison of CHO-R cAMP results with FRTL-5 cAMP results. The CHO-R value was 173. The FRTL-5 cut-off value was 153. Values below cutoff were as follows (FRTL-5 values): 110 (830), 113 (283), 116 (212), 152 (1100), 156 (388), and 161 (335). The average+/−SD values for the IgG Control (ICN), for the tests shown in FIG. 2 were 472+/−4015 (n=8).

FIG. 5 shows the linearity of the response to bTSH of the CHO-Rluc cells. In these experiments, dilutions of bTSH were tested. The RLU/sec values obtained are shown in Table 7, below.

TABLE 7

Results for bTSH Dilutions

| | μIU TSH.ml | | | | | |
|---|---|---|---|---|---|---|
| Results | 0 | 10 | 25 | 50 | 75 | 100 |
| RLU/sec | 0 | 5,921 | 20,227 | 34,426 | 54,396 | 62,206 |

It is contemplated that this linearity and sensitivity of response to bTSH will prove useful in the detection of blocking antibodies to the TSH receptor (e.g., those autoantibodies in patents with atrophic thyroiditis and Hashimoto's thyroiditis which block the TSH receptor, thereby preventing thyroid hormone production and release resulting in hypothyroidism). This Figure also provides at least a partial explanation of why the CHO-R cell line is not as sensitive to TSI from Graves' disease patients sera as the FRTL-5 cell line. In these results, the correlation coefficient (r) was 0.9925. The three S.D. (standard deviations) sensitivity was 1.3 μIU TSH/ml.

Example 9

Monitoring of Immune Responses

In these experiments, the immune response of vaccine recipients is measured and monitored. Although it is not intended that the present invention be so limited, this Example describes the monitoring of a subject's immune response to herpes simplex (HSV) vaccine.

Prior to administration of vaccine, a serum sample (i.e., preimmune serum) is collected from the subject for use as a baseline or control, and stored frozen until testing. Serum samples are also collected at periodic intervals following administration of the vaccine (e.g., 1-2 weeks, 1 month, 2 months post-vaccination, etc.). The sera are thawed as necessary, and used in an assay to determine the presence and quantity (i.e., titer) of neutralizing antibodies. Sera are serially diluted and mixed with known quantities of HSV. These samples are diluted in dilutent comprising Eagle's MEM with HBSS containing 2 mM glutamine, 2% FBS, and PEG (e.g., 6% PEG 8000). However, it is also contemplated that other diluents will find use in the present method, including diluents containing different concentrations and types of PEG, as appropriate for the virus and assay system used). These samples are added to cell monolayers containing cells capable of producing an enzyme such as (3-galactosidase upon infection with HSV (e.g., ELVIS™ cells, Diagnostic Hybrids). Following overnight incubation under standard cell culture conditions, the monolayers are lysed and the enzyme activity is measured using chromogenic or luminogenic methods.

A positive response to the vaccine is indicated by the lowest dilution of postvaccination serum which neutralizes HSV in the sample (i.e., as indicated by a low OD. or luminescence value, in comparison with the preimmune control).

In summary, the present invention provides numerous advances and advantages over the prior art, including the avoidance of radioactivity, in combination with the advantages of ease of use, reliability, sensitivity, specificity, cost-effectiveness, and reproducibility.

Example 10

Construction Chimeric TSH-R Plasmids

This example presents one embodiment of constructing a cell line comprising a chimeric TSH-R receptor for detecting Graves' disease autoantibodies.
Plasmid Construction A plasmid comprising a first nucleic acid sequences encoding a TSH-R chimeric receptor and a second nucleic acid sequence encoding a neomycin resistant gene was ligated to a luciferase gene and a glycoprotein hormone alpha subunit promoter.

Human Glycoprotein Alpha Subunit Promoter Cloning

Chromosomal DNA was isolated from human embryonic kidney cells using a QIAGEN RNA/DNA kit (QIAGEN Cat#14123.) Glycoprotein alpha subunit promoter fragments were amplified by PCR using the isolated chromosomal DNA as the PCR template and the 2 pairs of oligo-nucleotide primers shown below:

```
5' PCR primer:
5'-GAGCTC ATG TGT ATG GCT CAA TAA AAT TAC GTA CAA

AGT GAC AGC-3' (SEQ ID NO: 1)

3' PCR primer:
5'-AGATCT TCG TCT TAT GAG TTC TCA GTA ACT GCA GTA

TAA TGA AGT-3' (SEQ ID NO: 2).
```

A Sac I restriction site was added to the 5' end of the 5' PCR primer while a Bgl II restriction site was added to the 5' end of the 3' PCR primer (both shown as underlined sequence). For PCR amplification, BD Advantage 2 Polymerase Mix (BD Bioscience Palo Alto Calif.) was used and PCR reactions were performed in a thermal cycler (Eppendorf Mastercycler Personal, Germen.). Forty cycles were carried out at 94° C. for 30 seconds to denature the DNA. Samples were then annealed to the primers in the thermalcycler at 63° C. for 30 seconds, and the extension was induced at 68° C. for 1 minute 30 seconds per cycle. Two amplicons (1.2 kb and 0.6 kb) were cloned into the plasmid vector pcDNA2.1 (Invitrogen, Carlsbad, Calif.) and sequenced using the BigDye Terminator v3.0 Cycle Sequencing method on an ABI 377 automated sequencer (Davis Sequencing Inc.).

Construction of Plasmid pGFP/Luc

The human glycoprotein alpha subunit promoter was isolated from vector pcDNA2.1 by restriction cleavage with Sac I and Bgl II. The resulting 316 bp fragment was then subcloned into the Sac I/Bgl II site of the pGL2 enhancer plasmid (Promega, Madison, Wis.) for construction of a plasmid named pGHP/Luc.

Construction of Plasmid pMC4-neo

The neomycin resistance gene for antibiotic selection (positive clone selection) was isolated from vector pMC 1 (Stratagene Cedar Creek, Tex.) with restriction enzymes of XhoI and HicII. The resulting fragment was then subcloned into the XbaI site of plasmid pMC4 that contains the TSHR/LH chimeric receptor driven by the SV40 promoter (from Dr. Leonard Kohn.) The final plasmid was named pMC4-neo.

Construction of Plasmid pMC4-Bsd

The antibiotic selection gene Blastocidin, isolated from vector pCMV/Bsd (Invitrogen, Carlsbad, Calif.) with restriction enzymes XhoI and XbaI, was subcloned into the XbaI site of plasmid pMC4 which contains the TSHR/LH chimeric receptor. Tahara et al., "Immunoglobulins From Graves' Disease Patients Interact With Different Sites On TSH Receptor/LH/CG Receptor Chimeras Than Either TSH Or Immunoglobulins From Idiopathic Myxedema Patients" Biochem Biophys Res Comm 179:70-77 (1991). The final plasmid was named pMC4-Bsd.

Construction of Plasmid pMC4-GHP/Luc

The human glycoprotein alpha subunit promoter, with a firefly luciferase reporter gene, was isolated from vector pMC4/Luc following restriction cleavage by SmaI and AccI. The isolated DNA fragment was then subcloned into the PfoI site of pMC4-neo plasmid. The final plasmid was named pMV4-GHP/Luc.

Example 11

Mammalian Cell Selection

Seven different mammalian cell lines were tested to select the cell line that had the lowest cyclic AMP basal level and highest potential inducible levels. The results demonstrated that the CHO and RD cells showed the lowest cyclic AMP basal activity and the highest potential inducible level. This empirical research approach maximizes the assay sensitivity by proper selection of cell culture type. For example, a lower the cyclic AMP basal level increases the sensitivy of the luciferase assay. Also, the highest induced expression of cyclic AMP improves the accuracy of the luciferase assay.

Example 12

Transfection/Selection of a CHO Cell Line with Chimeric TSH-R Plasmid

This example describes the permanently transfection of CHO cells.

Chinese Hamster Ovary (CHO-K1; ATCC Number: CCL-61, Manassas Va.) cell line was transfected with a linearized (Xmn1) pMC4-GPH/Luciferase plasmid using HyFect® (Denville Scientific, Metuchen, N.J.) according to the manufacturer's instructions. The CHO-K1 cells were then grown in Ham's F12 Medium with 10% (v/v) fetal bovine serum and nine essential amino acids at 37° C. in a humidified atmosphere containing 5% $CO_2$. Twenty four hours after the transfection, the cells were combined and planted into a 96 well plate and selected with 0.5 mg/ml G418 in Ham's F12 Medium with 10% FBS.

Example 13

Transfection/Selection of an RD Cell Line with Chimeric TSH-R Plasmid

This example describes the transfection of a Human Rhabdomyosarcoma (RD) (ATCC Number: CCL-136.) cell line with two plasmids, pGHP/Luc and pMC4-Bsd, in series to facilitate detection.

RD cells were transfected with the linearized pGPH/Luc (Sca1) plasmid using HyFect (Denville Scientific, Metuchen, N.J.) according to the manufacturer's instructions. The cells were selected with 0.5 mg/ml of neomycin. The optimal clone from this transfection and selection was then transfected with the linearized plasmid pMC4-Bsd. After transfection, the cells were selected with both neomycin (0.5 mg/ml) and blasticidin (5 μg/ml.) to produce the final RD recombinant cell line.

All CHO and RD antibiotic resistant clones were tested with TSI-positive and normal serum to select the clone which can be used for the detection of TSI. The TSI induction positive clone was subjected to the limiting dilution cloning to further select a single clone.

The final clones have the ability to diagnose Graves' disease and/or monitor the drug treatment of patients with Graves' disease with higher sensitivity than the current product on the market. These cell lines show good stability, having been passaged more than ten times, and continue to show very similar performance characteristics.

Example 14

Induction of Cell Lines with TSI Containing Serum

CHO cells from freezer vials were diluted and grown in growth media (Ham's F12 Medium with 10 (v/v) % fetal bovine serum and nine essential amino acids) for 16 hours at 37° C. and 5% $CO_2$. After 16 hours the media was removed and theh CHO cells were rinsed and refed with 1000 well "starvation" HBSS medium. The CHO cells were then incubated for 22-24 hours. Following incubation the media was removed and CHO cells were rinsed and refed with 100 μl/well reaction buffer. The CHO cells were then induced with a 1:11 dilution of patient serum in reaction buffer containing BSA, PEG, sucrose, glucose, and salts (Diagnostic Hybrids Catalog number 40-300500) for 4 hours at 37° C. and 5% $CO_2$.

RD cells were grown in EMEM with 10 (v/v) % fetal bovine serums at 37° C. and 5% $CO_2$ for 16-24 hours. RD cells were then directly induced with patient serum in reaction buffer (Diagnostic Hybrids Catalog number 40-300500) for 4 hours at 37° C. and 5% $CO_2$.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in diagnostics, cell culture, and•or related fields are intended to be within the scope of the following claims.

I claim:

1. A recombinant chimeric thyroid stimulating hormone (TSH) receptor polypeptide encoded by nucleotides 45-2234 of SEQ ID NO:3.

2. A recombinant polypeptide consisting of a chimeric thyroid stimulating hormone (TSH) receptor, wherein said chimeric TSH receptor consists of:
   - an N-terminal portion of a human thyroid stimulating hormone receptor (hTSHR), wherein the N-terminal portion of the hTSHR consists of the amino acid sequence encoded by nucleotides 45-827 of SEQ NO:3;
   - a portion of a rat luteinizing hormone chorionic gonadotropin receptor (rLH/CGR), wherein the portion of the rLH/CGR consists of the amino acid sequence encoded by nucleotides 828 to 1046 of SEQ ID NO:3; and
   - a C-terminal portion of said hTSHR, wherein the C-terminal portion of the hTSHR consists of the amino acid sequence encoded by nucleotides 1047-2234 of SEQ ID NO:3.

3. A recombinant nucleic acid sequence which encodes said recombinant chimeric thyroid stimulating hormone (TSH) receptor polypeptide of claim 2.

4. A nucleotide vector comprising a recombinant nucleic acid sequence which encodes said recombinant chimeric thyroid stimulating hormone (TSH) receptor polypeptide of claim 2.

5. The vector of claim 4, further comprising a promoter operably linked to the recombinant nucleic acid sequence.

6. The vector of claim 5, wherein the promoter comprises a glycoprotein alpha subunit promoter.

7. The vector of claim 4, further comprising a luciferase nucleic acid sequence.

8. The vector of claim 7, wherein the luciferase nucleic acid sequence is derived from a firefly.

9. A cell line comprising a transfected vector, wherein the vector comprises the nucleic acid sequence of claim 3.

10. The cell line of claim 9, wherein the cell line is stably transfected with the vector.

11. The cell line of claim 9, wherein the cell line is selected from the group consisting of CHO cells and RD cells.

12. A kit comprising the nucleic acid sequence of claim 3.

13. The kit of claim 12, further comprising a cell line which is transfected with the nucleic acid sequence.

14. The kit of claim 13, further comprising polyethylene glycol.

15. The kit of claim 12, wherein the nucleic acid sequence is integrated into a vector.

16. The kit of claim 15, wherein the vector further comprises a luciferase gene and a promoter wherein the promoter is operably linked to the nucleic acid sequence.

* * * * *

SEQUENCE LISTING

```
<160> NUMBER OF SEQ ID NOS: 10

<210> SEQ ID NO 1
<211> LENGTH: 45
<212> TYPE: DNA
<213> ORGANISM: Artificial Sequence
<220> FEATURE:
<223> OTHER INFORMATION: Synthetic

<400> SEQUENCE: 1
gagctcatgt gtatggctca ataaaattac gtacaaagtg acagc              45

<210> SEQ ID NO 2
<211> LENGTH: 45
<212> TYPE: DNA
<213> ORGANISM: Artificial Sequence
<220> FEATURE:
<223> OTHER INFORMATION: Synthetic

<400> SEQUENCE: 2
agatcttcgt cttatgagtt ctcagtaact gcagtataat gaagt              45

<210> SEQ ID NO 3
<211> LENGTH: 2324
<212> TYPE: DNA
<213> ORGANISM: Artificial Sequence
<220> FEATURE:
<223> OTHER INFORMATION: Synthetic

<400> SEQUENCE: 3
ggcgatttcg gaggatggag aaatagcccc gagtcccgtg gaaaatgagg ccggcggact    60
tgctgcagct ggtgctgctg ctcgacctgc ccagggacct gggcggaatg gggtgttcgt   120
ctccaccctg cgagtgccat caggaggagg acttcagagt cacctgcaag gatattcaac   180
gcatccccag cttaccgccc agtacgcaga ctctgaagct tattgagact cacctgagaa   240
```

-continued

```
ctattccaag tcatgcattt tctaatctgc ccaatatttc cagaatctac gtatctatag    300
atgtgactct gcagcagctg gaatcacact ccttctacaa tttgagtaaa gtgactcaca    360
tagaaattcg gaataccagg aacttaactt acatagaccc tgatgccctc aaagagctcc    420
ccctcctaaa gttccttggc attttcaaca ctggacttaa aatgttccct gacctgacca    480
aagtttattc cactgatata ttctttatac ttgaaattac agacaaccct tacatgacgt    540
caatccctgt gaatgctttt cagggactat gcaatgaaac cttgacactg aagctgtaca    600
acaatggctt tacttcagtc caaggatatg ctttcaatgg gacaaagctg gatgctgttt    660
acctaaacaa gaataaatac ctgacagtta ttgacaaaga tgcatttgga ggagtataca    720
gtggaccaag cttgctggac gtgtctcaaa ccagtgtcac tgcccttcca tccaaaggcc    780
tggagcacct gaaggaactg atagcaagaa acacctggac tcttaagaca ctgccctcca    840
aagaaaaatt cacgagcctc ctggtcgcca cgctgaccta ccccagccac tgctgcgcct    900
tcagtaattt gccgaagaaa gaacagaatt tttcattttc cattttttgaa aacttctcca    960
aacaatgcga aagcacagtt agaaaagcag ataacgagac gctttattcc gccatctttg   1020
aggagaatga actcagtggc tgggatgagc tcaaaaaccc ccaggaagag actctacaag   1080
cttttgacag ccattatgac tacaccatat gtggggacag tgaagacatg gtgtgtaccc   1140
ccaagtccga tgagttcaac ccgtgtgaag acataatggg ctacaagttc ctgagaattg   1200
tggtgtggtt cgttagtctg ctggctctcc tgggcaatgt cttttgtcctg cttattctcc   1260
tcaccagcca ctacaaactg aacgtccccc gctttctcat gtgcaacctg gcctttgcgg   1320
atttctgcat ggggatgtac ctgctcctca tcgcctctgt agacctctac actcactctg   1380
agtactacaa ccatgccatc gactggcaga caggccctgg gtgcaacacg gctggttttct   1440
tcactgtctt tgcaagcgag ttatcggtgt atacgctgac ggtcatcacc ctggagcgct   1500
ggtatgccat caccttcgcc atgcgcctgg accggaagat ccgcctcagg cacgcatgtg   1560
ccatcatggt tggggctggg tttgctgct tccttctcgc cctgcttcct ttggtgggaa   1620
taagtagcta tgccaaagtc agtatctgcc tgcccatgga caccgagacc cctcttgctc   1680
tggcatatat tgttttttgtt ctgacgctca acatagttgc cttcgtcatc gtctgctgct   1740
gttatgtgaa gatctacatc acagtccgaa atccgcagta caacccaggg gacaaagata   1800
ccaaaattgc caagagggatg gctgtgttga tcttcaccga cttcatatgc atggccccaa   1860
tctcattcta tgctctgtca gcaattctga acaagcctct catcactgtt agcaactcca   1920
aaatcttgct ggtactcttc tatccactta actcctgtgc caatccattc ctctatgcta   1980
ttttcaccaa ggccttccag agggatgtgt tcatcctact cagcaagttt ggcatctgta   2040
aacgccaggc tcaggcatac cggggggcaga gggttcctcc aaagaacagc actgatattc   2100
aggttcaaaa ggttacccac gacatgaggc agggtctcca acatggaa gatgtctatg   2160
aactgattga aaactcccat ctaacccaa agaagcaagg ccaaatctca gaagagtata   2220
tgcaaacggt tttgtaagtt aacactacac tactcacaat ggtagggaa cttacaaaat   2280
aatagtttct tgaatatgca ttccaatccc atgacacccc caac                     2324
```

<210> SEQ ID NO 4
<211> LENGTH: 304
<212> TYPE: DNA
<213> ORGANISM: Homo sapiens

<400> SEQUENCE: 4

```
atgtgtatgg ctcaataaaa ttacgtacaa agtgacagcg tactctcttt tcatgggctg    60
accttgtcgt caccatcacc tgaaaatggc tccaaacaaa aatgacctaa gggttgaaac   120
aagataagat caaattgacg tcatggtaaa aattgacgtc atggtaatta caccaagtac   180
ccttcaatca ttggatggaa tttcctgttg atcccagggc ttagatgcag gtggaaacac   240
tctgctggta taaaagcagg tgacgacttc attatactgc agttactgag aactcataag   300
acga                                                                304
```

```
<210> SEQ ID NO 5
<211> LENGTH: 337
<212> TYPE: DNA
<213> ORGANISM: Artificial Sequence
<220> FEATURE:
<223> OTHER INFORMATION: Synthetic

<400> SEQUENCE: 5
attcgccctt gagctcatgt gtatggctca ataaaattac gtacaaagtg acagcgtact    60
ctcttttcat gggctgacct tgtcgtcacc atcacctgaa aatggctcca acaaaaatg   120 acctaagggt tgaaacaaga taagatcaaa ttgacgtcat ggtaaaaatt gacgtcatgg   180
taattacacc aagtacccct tcaatcattgg atggaatttc ctgttgatcc cagggcttag   240
atgcaggtgg aaacactctg ctggtataaa agcaggtgag gacttcatta tactgcagtt   300
actgagaact cataagacga agatctaagg gcgaatt                            337
```

```
<210> SEQ ID NO 6
<211> LENGTH: 85
<212> TYPE: PRT
<213> ORGANISM: Bos taurus

<400> SEQUENCE: 6

Gln Thr Leu Ile Ala Thr Ser Ser Tyr Ser Leu Lys Lys Leu Pro Ser
1               5                   10                  15

Arg Glu Lys Phe Ala Asn Leu Leu Asp Ala Thr Leu Thr Tyr Pro Ser
            20                  25                  30

His Cys Cys Ala Phe Arg Asn Val Pro Thr Lys Glu Gln Asn Phe Ser
        35                  40                  45

Phe Ser Ile Ser Lys Asn Phe Pro Lys Gln Cys Glu Ser Thr Val Arg
    50                  55                  60

Lys Gln Asn Asn Glu Thr Leu Tyr Pro Ala Ile Phe Ala Glu Ser Gly
65                  70                  75                  80

Gln Ser Gly Trp Asp
            85
```

```
<210> SEQ ID NO 7
<211> LENGTH: 173
<212> TYPE: PRT
<213> ORGANISM: Bos taurus

<400> SEQUENCE: 7

Ile Leu Ile Leu Asn Thr Lys Asn Leu Leu His Ile Glu Asp Gly Ala
1               5                   10                  15

Phe Arg Asn Leu Pro Arg Leu Lys Tyr Leu Ser Ile Cys Asn Thr Gly
            20                  25                  30

Ile Ile Glu Phe Pro Asp Leu Thr Gln Ile Phe Ser Ser Glu Ala His
        35                  40                  45

Phe Ile Leu Glu Leu Cys Asp Asn Leu Arg Met Thr Thr Ile Pro Gln
    50                  55                  60
```

```
Asn Ala Phe Arg Gly Met Ser Asn Glu Ser Leu Thr Leu Lys Leu Tyr
 65                  70                  75                  80

Lys Asn Gly Phe Glu Asp Ile His Ser His Ala Phe Asn Gly Thr Lys
                 85                  90                  95

Leu Asn Gln Leu Ile Leu Lys Asp Asn Lys Asn Leu Arg Arg Ile His
            100                 105                 110

Asn Asp Ala Leu Arg Gly Ala Ile Gly Pro Asp Val Leu Asp Ile Ser
            115                 120                 125

Ser Thr Ala Leu Glu Ser Leu Pro Ser Tyr Gly Leu Glu Ala Ile Gln
            130                 135                 140

Val Leu Asn Gly Met Ser Ser Tyr Ser Leu Lys Arg Leu Pro Pro Leu
145                 150                 155                 160

Asp Lys Phe Ser Ser Leu Leu Glu Ala Val Leu Thr Tyr
                165                 170
```

<210> SEQ ID NO 8
<211> LENGTH: 728
<212> TYPE: PRT
<213> ORGANISM: Bos taurus

<400> SEQUENCE: 8

```
Met Leu Pro Ala Leu Pro Leu Leu Leu Pro Ala Leu Leu Pro Gly
  1               5                  10                  15

Ala Gly Gly Gly Arg Cys Pro Gln Arg Cys Ala Cys Thr Gln Pro Ala
                 20                  25                  30

Leu Arg Cys Pro Thr Pro Pro Gly Ala Arg Pro Ala Pro Ala Arg
             35                  40                  45

Ala Ser Phe Thr His Leu Pro Val Lys Val Ile Pro Ser His Ala Phe
         50                  55                  60

Glu Gly Leu Arg Asp Ala Phe Ile Ile Glu Ile Ser Gln Ser Asp Ser
 65                  70                  75                  80

Leu Glu Arg Ile Glu Ala Ser Ala Phe Asp Ser Leu Pro Ala Leu Ser
                 85                  90                  95

Glu Ile Leu Ile Leu Asn Thr Lys Asn Leu Leu His Ile Glu Asp Gly
            100                 105                 110

Ala Phe Arg Asn Leu Pro Arg Leu Lys Tyr Leu Ser Ile Cys Asn Thr
            115                 120                 125

Gly Ile Ile Glu Phe Pro Asp Leu Thr Gln Ile Phe Ser Ser Glu Ala
            130                 135                 140

His Phe Ile Leu Glu Leu Cys Asp Asn Leu Arg Met Thr Thr Ile Pro
145                 150                 155                 160

Gln Asn Ala Phe Gln Gly Met Ser Asn Glu Ser Leu Thr Leu Lys Leu
                165                 170                 175

Tyr Lys Asn Gly Phe Glu Asp Ile His Ser His Ala Phe Asn Gly Thr
                180                 185                 190

Lys Leu Asn Gln Leu Ile Leu Lys Asp Asn Lys Asn Leu Arg Arg Ile
            195                 200                 205

His Asn Asp Ala Leu Arg Gly Ala Thr Gly Pro Asp Val Leu Asp Ile
        210                 215                 220

Ser Ser Thr Ala Leu Glu Ser Leu Pro Ser Tyr Gly Leu Glu Ala Ile
225                 230                 235                 240

Gln Val Leu Asn Ala Met Ser Ser Tyr Ser Leu Lys Arg Leu Pro Pro
                245                 250                 255

Leu Asp Lys Phe Ser Ser Leu Leu Glu Ala Val Leu Thr Tyr Pro Ser
```

-continued

```
                260                 265                 270
His Cys Cys Ala Phe Gln Asn Leu Arg Thr Glu Lys Gln Asn Ser Leu
            275                 280                 285
Leu Ser Ile Phe Asp Asn Phe Ser Lys Gln Cys Glu Ser Thr Met Arg
        290                 295                 300
Lys Pro Ala Ser Glu Val Phe Tyr Arg Asp Ala Ser Ser Asn Thr Ser
305                 310                 315                 320
Leu Trp Pro Ala Glu Lys His Met Tyr Pro Leu Glu Thr Gly Glu Glu
                325                 330                 335
Ala Phe Pro Tyr Ser Tyr Ser Thr Val Phe Tyr Glu Asp Glu Met Thr
            340                 345                 350
Gly Phe Asp Phe Glu Tyr Asp Phe Cys Gln Pro Lys Ile Leu Thr Cys
        355                 360                 365
Thr Pro Glu Pro Asp Ala Phe Asn Pro Cys Glu Asp Ile Leu Gly Tyr
    370                 375                 380
Ser Phe Leu Arg Val Leu Ile Trp Phe Ile Asn Ile Leu Ala Leu Ala
385                 390                 395                 400
Gly Asn Phe Ile Val Leu Leu Val Leu Ile Thr Ser His Tyr Lys Leu
                405                 410                 415
Thr Val Pro Arg Phe Leu Met Cys Asn Leu Ser Phe Ala Asp Phe Cys
            420                 425                 430
Met Gly Leu Tyr Leu Leu Leu Ile Ala Ser Val Asp Ala Gln Thr Ser
        435                 440                 445
Gly Gln Tyr Tyr Asn His Ala Ile Asp Trp Gln Thr Gly Ser Gly Cys
    450                 455                 460
Ser Thr Ala Gly Phe Phe Thr Val Phe Ala Ser Glu Leu Ser Val Tyr
465                 470                 475                 480
Thr Leu Thr Val Ile Thr Ile Glu Arg Trp His Thr Ile Thr Tyr Ala
                485                 490                 495
Met Gln Leu Asp Arg Lys Leu Arg Leu Arg His Ala Val Pro Ile Met
            500                 505                 510
Leu Gly Gly Trp Val Phe Ser Ile Leu Ile Ala Val Leu Pro Leu Leu
        515                 520                 525
Gly Val Ser Ser Tyr Met Lys Val Ser Ile Cys Leu Pro Met Asp Ile
    530                 535                 540
Glu Thr Gly Leu Ser Gln Ala Tyr Ile Leu Leu Ile Leu Met Leu Asn
545                 550                 555                 560
Val Ile Ala Phe Leu Val Ile Cys Ala Cys Tyr Ile Lys Ile Tyr Val
                565                 570                 575
Ala Val Gln Asn Pro Glu Leu Val Ala Asn Lys Asp Thr Lys Ile
            580                 585                 590
Ala Lys Arg Met Ala Ile Leu Ile Phe Thr Asp Phe Thr Cys Met Ala
        595                 600                 605
Pro Ile Ser Phe Phe Ala Ile Ser Ala Ala Ile Lys Val Pro Leu Ile
    610                 615                 620
Thr Val Thr Asn Ser Lys Ile Leu Leu Val Leu Phe Tyr Pro Val Asn
625                 630                 635                 640
Ser Cys Ala Asn Pro Phe Leu Tyr Ala Ile Phe Thr Lys Ala Phe Gln
                645                 650                 655
Arg Asp Phe Phe Leu Leu Met Ser Lys Leu Gly Cys Cys Lys Ser Arg
            660                 665                 670
Ala Glu Leu Tyr Arg Val Asn Tyr Phe Ser Ala Tyr Thr Pro Asn Cys
        675                 680                 685
```

-continued

Lys Asn Gly Ser Ser Ala Pro Gly Pro Ser Lys Ala Ser Gln Ala Leu
            690                 695                 700

Leu Leu Leu Ser Ala Ser Glu Lys Leu Cys Lys Thr Arg Arg Ser Thr
705                 710                 715                 720

Lys Lys Ser Gln Pro Glu Cys Gln
                725

<210> SEQ ID NO 9
<211> LENGTH: 58
<212> TYPE: PRT
<213> ORGANISM: Bos taurus

<400> SEQUENCE: 9

Met Gly Arg Arg Val Pro Ala Leu Arg Gln Leu Leu Val Leu Ala Met
1               5                   10                  15

Leu Val Leu Lys Gln Ser Gln Leu His Ser Pro Glu Leu Ser Gly Ser
                20                  25                  30

Arg Cys Pro Glu Pro Cys Asp Cys Ala Pro Asp Gly Ala Leu Arg Cys
            35                  40                  45

Pro Gly Pro Arg Ala Gly Leu Ala Arg Leu
        50                  55

<210> SEQ ID NO 10
<211> LENGTH: 701
<212> TYPE: PRT
<213> ORGANISM: Bos taurus

<400> SEQUENCE: 10

Met Gly Arg Pro Ser Leu Ala Leu Arg Leu Leu Ala Leu Leu Leu
1               5                   10                  15

Leu Pro Pro Pro Ala Pro Leu Leu Trp Ala Leu Arg Pro Ala Pro Cys
                20                  25                  30

Pro Glu Pro Cys Ser Cys Pro Pro Asp Gly Ala Leu Arg Cys Pro Gly
            35                  40                  45

Pro Gln Ala Gly Leu Ser Arg Leu Ser Leu Thr Tyr Leu Pro Ile Lys
        50                  55                  60

Val Ile Pro Ser Gln Ala Phe Arg Gly Leu Asn Glu Val Ile Lys Ile
65                  70                  75                  80

Glu Ile Ser Gln Ser Asp Ser Leu Glu Lys Ile Glu Ala Asn Ala Phe
                85                  90                  95

Asp Asn Leu Leu Asn Leu Ser Glu Ile Leu Ile Gln Asn Thr Lys Asn
            100                 105                 110

Leu Val His Ile Glu Ala Gly Ala Phe Thr Asn Leu Pro Arg Leu Lys
        115                 120                 125

Tyr Leu Ser Ile Cys Asn Thr Gly Ile His Lys Leu Pro Asp Val Thr
    130                 135                 140

Lys Ile Phe Ser Ser Glu Phe Asn Phe Ile Leu Glu Ile Cys Asp Asn
145                 150                 155                 160

Leu His Ile Thr Thr Ile Pro Arg Asn Ala Phe Gln Gly Met Asn Asn
                165                 170                 175

Glu Ser Ile Thr Leu Lys Leu Tyr Gly Asn Gly Phe Glu Glu Ile Gln
            180                 185                 190

Ser His Ala Phe Asn Gly Thr Thr Leu Ile Ser Leu Glu Leu Lys Glu
        195                 200                 205

Asn Ala Arg Leu Glu Lys Met His Asn Asp Ala Phe Arg Gly Ala Thr
    210                 215                 220

```
Gly Pro Ser Ile Leu Asp Ile Ser Ser Thr Lys Leu Gln Ala Leu Pro
225                 230                 235                 240

Thr Tyr Gly Leu Glu Ser Ile Gln Thr Leu Ile Ala Thr Ser Ser Tyr
            245                 250                 255

Ser Leu Lys Lys Leu Pro Ser Arg Glu Lys Phe Thr Asn Leu Leu Asp
            260                 265                 270

Ala Thr Leu Thr Tyr Pro Ser His Cys Cys Ala Phe Arg Asn Leu Pro
            275                 280                 285

Thr Asn Glu Gln Asn Phe Ser Phe Ser Ile Phe Lys Asn Phe Ser Lys
290                 295                 300

Gln Cys Glu Ser Thr Ala Arg Arg Pro Asn Asn Glu Thr Leu Tyr Ser
305                 310                 315                 320

Ala Ile Phe Ala Glu Ser Glu Leu Ser Gly Trp Asp Tyr Asp Tyr Gly
            325                 330                 335

Phe Cys Leu Pro Lys Thr Leu Gln Cys Ala Pro Glu Pro Asp Ala Phe
            340                 345                 350

Asn Pro Cys Glu Asp Ile Met Gly Tyr Asn Phe Leu Arg Val Leu Ile
            355                 360                 365

Trp Leu Ile Asn Ile Leu Ala Ile Thr Gly Asn Val Thr Val Leu Phe
370                 375                 380

Val Leu Leu Thr Ser Arg Tyr Lys Leu Thr Val Pro Arg Phe Leu Met
385                 390                 395                 400

Cys Asn Leu Ser Phe Ala Asp Phe Cys Met Gly Leu Tyr Leu Leu Leu
                405                 410                 415

Ile Ala Ser Val Asp Ala Gln Thr Lys Gly Gln Tyr Tyr Asn His Ala
                420                 425                 430

Ile Asp Trp Gln Thr Gly Ser Gly Cys Ser Ala Ala Gly Phe Phe Thr
                435                 440                 445

Val Phe Ala Ser Glu Leu Ser Val Tyr Thr Leu Thr Val Ile Thr Leu
450                 455                 460

Glu Arg Trp His Thr Ile Thr Tyr Ala Ile Gln Leu Asp Gln Lys Leu
465                 470                 475                 480

Arg Leu Lys His Ala Ile Pro Val Met Leu Gly Gly Trp Leu Phe Ser
                485                 490                 495

Thr Leu Ile Ala Val Leu Pro Leu Val Gly Val Ser Asn Tyr Met Lys
                500                 505                 510

Val Ser Ile Cys Leu Pro Met Asp Val Glu Ser Thr Leu Ser Gln Val
                515                 520                 525

Tyr Ile Leu Thr Ile Leu Ile Leu Asn Val Met Ala Phe Ile Ile Ile
                530                 535                 540

Cys Ala Cys Tyr Ile Lys Ile Tyr Phe Ala Val Gln Asn Pro Glu Leu
545                 550                 555                 560

Met Ala Thr Asn Lys Asp Thr Lys Ile Ala Lys Lys Met Ala Val Leu
                565                 570                 575

Ile Phe Thr Asp Phe Thr Cys Met Ala Pro Ile Ser Phe Phe Ala Ile
                580                 585                 590

Ser Ala Ala Phe Lys Val Pro Leu Ile Thr Val Thr Asn Ser Lys Val
                595                 600                 605

Leu Leu Val Leu Phe Tyr Pro Val Asn Ser Cys Ala Asn Pro Phe Leu
                610                 615                 620

Tyr Ala Ile Phe Thr Lys Ala Phe Gln Arg Asp Phe Phe Leu Leu Leu
625                 630                 635                 640
```

```
Ser Lys Phe Gly Cys Cys Lys Tyr Arg Ala Glu Leu Tyr Arg Arg Lys
            645             650             655

Asp Phe Ser Ala Tyr Ile Ser Asn Cys Lys Asn Gly Phe Thr Gly Ser
            660             665             670

Asn Lys Pro Ser Arg Ser Thr Phe Lys Leu Thr Thr Leu Gln Cys Gln
        675             680             685

Tyr Ser Ala Val Leu Asp Lys Thr Cys Tyr Lys Glu Cys
        690             695             700
```